US010526607B2

(12) United States Patent
Jalkanen et al.

(10) Patent No.: US 10,526,607 B2
(45) Date of Patent: Jan. 7, 2020

(54) CELL AND THERAPEUTICAL AND DIAGNOSTICAL METHODS BASED THEREON

(71) Applicant: FARON PHARMACEUTICALS OY, Turku (FI)

(72) Inventors: Sirpa Jalkanen, Piispanristi (FI); Marko Salmi, Turku (FI); Markku Jalkanen, Piispanristi (FI)

(73) Assignee: FARON PHARMACEUTICALS OY, Turku (FI)

( * ) Notice: Subject to any disclaimer, the term of this patent is extended or adjusted under 35 U.S.C. 154(b) by 0 days.

(21) Appl. No.: 14/224,374

(22) Filed: Mar. 25, 2014

(65) Prior Publication Data
US 2014/0294760 A1 Oct. 2, 2014

Related U.S. Application Data

(63) Continuation of application No. 13/262,088, filed as application No. PCT/FI2010/050266 on Apr. 6, 2010, now Pat. No. 8,722,045.

(30) Foreign Application Priority Data

Apr. 22, 2009 (FI) ..................................... 20090161

(51) Int. Cl.
*G01N 33/574* (2006.01)
*C12N 15/113* (2010.01)
*C07K 16/28* (2006.01)
*A61K 31/58* (2006.01)
*A61K 35/15* (2015.01)
*A61K 38/17* (2006.01)
*A61K 38/20* (2006.01)
*C12N 15/115* (2010.01)
*C12Q 1/6883* (2018.01)
*C12Q 1/6886* (2018.01)

(52) U.S. Cl.
CPC .......... *C12N 15/1138* (2013.01); *A61K 31/58* (2013.01); *A61K 35/15* (2013.01); *A61K 38/17* (2013.01); *A61K 38/202* (2013.01); *A61K 38/2026* (2013.01); *C07K 16/28* (2013.01); *C12N 15/115* (2013.01); *C12Q 1/6883* (2013.01); *C12Q 1/6886* (2013.01)

(58) Field of Classification Search
None
See application file for complete search history.

(56) References Cited

U.S. PATENT DOCUMENTS

| 7,910,097 | B2 | 3/2011 | Jalkanen et al. | |
| 2003/0211498 | A1 | 11/2003 | Morin et al. | |
| 2004/0191783 | A1* | 9/2004 | Leclercq | C12Q 1/6837 506/16 |
| 2005/0069888 | A1* | 3/2005 | Jalkanen | C07K 16/28 435/6.16 |
| 2008/0267958 | A1 | 10/2008 | Jalkanen et al. | |
| 2010/0055686 | A1* | 3/2010 | Burdach | C12Q 1/6886 435/6.11 |
| 2010/0070191 | A1* | 3/2010 | Gold | G01N 33/57423 702/19 |
| 2011/0119776 | A1* | 5/2011 | Wong | G01N 33/57423 800/10 |

FOREIGN PATENT DOCUMENTS

| EP | 1661915 A1 | 5/2006 |
| WO | 2000/0055173 A1 | 9/2000 |
| WO | 03057130 A2 | 7/2003 |
| WO | 2008019872 | 2/2008 |
| WO | 2008097908 A2 | 8/2008 |
| WO | 2008097908 A3 | 8/2008 |

OTHER PUBLICATIONS

Poblete-Gutierrez et al, Experimental Dermatology, 18:317, P254A, Mar. 2009).*
Kzhyshkowska, J. et al., "Alternatively Activated Macrophages Regulate Extracellular Levels of the Hormone Placental Lactogen via Receptor-Mediated Uptake and Transcytosis," The Journal of Immunology, 2008, vol. 180, pp. 3028-3037.
Palani et al., "Stabilin-1/CLEVER-1, a type 2 macrophage marker, is an adhesion and scavenging molecule on human placental macrophages," Eur. J. Immunol., 41: 2052-63 (2011).
Press Release, "Faron updates pipeline development plans", Mar. 25, 2009, 2 pgs.
Press Release, "Taking innovations further", Jan. 1, 2005, 7 pgs.
Conway et al., "A Clever molecule that regulates lymphoctye trafficking", Blood, vol. 104, No. 13, Dec. 15, 2004, pp. 3840-3841.
The Extended European Search Report cited in Application No. 17197919.8-1116, dated Mar. 9, 2018, 9 pgs.
Office Action cited in Canadian Application No. 3,022,659, dated Dec. 5, 2018, 5 pages.
Kzhyshkowska et al., "Stabilin-1, a homeostatic scavenger receptor with multiple functions", J. Cell. Mol. Med., vol. 10, No. 3, pp. 635-649, 2006.
Byers, T., CA Journal, vol. 49, No. 6, Nov./Dec. 1999.
Ben-Efraim, Tumor Biology 1999, 20: 1-24.
Frazer, I., Expert Opinion on Pharmacotherapy 2004, 5: 2427-2434.
Gura, Science, 1997, 278: 1041-1042.
Kaiser, Science, 2006, 313, 1370.

(Continued)

*Primary Examiner* — Mark Halvorson
(74) *Attorney, Agent, or Firm* — Rothwell, Figg, Ernst & Manbeck, P.C.

(57) ABSTRACT

The invention relates to a novel cell derived from the human body, where said cell comprises a Clever-1 receptor; to a method for affecting the immune system of an individual and for treatment of diseases or conditions related to the function of the immune system and to methods for screening of cancer patients that may respond to an anti-Clever-1 therapy or for diagnosing of a pregnancy complication or for estimating the risk of such complication in a pregnant woman.

6 Claims, 10 Drawing Sheets
Specification includes a Sequence Listing.

(56) References Cited

OTHER PUBLICATIONS

Granziero et al., European Journal of Immunology, 1999, 29: 1127-1138.

Irjala H. et al., "Mannose Receptor (MR) and Common Lymphatic Endothelial and Vascular Endothelial Receptor (CLEVER)-1 Direct the Binding of Cancer Cells to the Lymph Vessel Endothelium," Cancer Research, Aug. 2003, vol. 63, pp. 4671-4676.

Kzhyshkowska, J., "Die Rolle von Makrophagen in Entzundungen and Tumoren: neue Stabilin-1-vermittelte Prozesse," Aktuelle Dermatologie, Mar. 2008, vol. 34, No. 3, pp. 72-84.

Ammar, A. et al., "Role of CLEVER-1 in Breast Cancer Metastasis," Breast Cancer Research, May 2008, vol. 10, Suppl. 2, p. 35.

Karikoski, M. et al., "Clever-1/Stabilin-1 Regulates Lymphocyte Migration Within Lymphatics and Leukocyte Entrance to Sites of Inflammation," European Journal of Immunology, Dec. 2009, vol. 39, No. 12, pp. 3477-3487.

* cited by examiner

A

B

C anti-Clever-1 anti-CD14 negat co, NS-1 negat co, 3G6

Non transfected cells – Day 2

Control      anti-Clever-1

52%

Negative control transfected – Day 2

53%

Clever-1 siRNA transfected – Day 2

25%

Pooled Clever-1 siRNA transfected – Day 2

14%

CELL AND THERAPEUTICAL AND DIAGNOSTICAL METHODS BASED THEREON

CROSS-REFERENCE TO RELATED APPLICATIONS

The present application is continuation of U.S. patent application Ser. No. 13/262,088 filed 29 Sep. 2011, which in turn is a national stage filing under 35 U.S.C. § 371 of PCT/FI2010/050266, filed 6 Apr. 2010, which in turn claims priority to Finnish Patent Application No. 20090161, filed 22 Apr. 2009, each of which is incorporated herein by reference.

SEQUENCE SUBMISSION

The present application is being filed along with a Sequence Listing in electronic format. The Sequence Listing is entitled 3100117SequenceListing.txt, created on 19 Mar. 2014 and is 38 kb in size. The information in the electronic format of the Sequence Listing is incorporated herein by reference in their entirety.

FIELD OF THE INVENTION

This invention relates to a novel cell derived from the human body, where said cell comprises a Clever-1 receptor; to a method for affecting the immune system of an individual and for treatment of diseases or conditions related to the function of the immune system and to methods for screening of cancer patients that may respond to an anti-Clever-1 therapy or for diagnosing of a pregnancy complication or for estimating the risk of such complication in a pregnant woman.

BACKGROUND OF THE INVENTION

The publications and other materials used herein to illuminate the background of the invention, and in particular, cases to provide additional details respecting the practice, are incorporated by reference.

CLEVER-1 is a protein disclosed in WO 03/057130, Common Lymphatic Endothelial and Vascular Endothelial Receptor-1. It is a binding protein that mediates adhesion of lymphocytes (and malignant tumor cells) to endothelium in both the systemic vasculature and in the lymphatics. By blocking the interaction of Clever-1 and its lymphocyte substrate it is possible to simultaneously control lymphocyte recirculation and lymphocyte migration, and related conditions such as inflammation, at the site of lymphocyte influx into, and efflux from, the tissues. WO 03/057130 also discloses that Clever-1 mediates binding of other types of leukocytes such as monocytes and granulocytes to HEV-like vessels. Thus, by blocking the interaction of Clever-1 and malignant tumor cells it became possible to control metastasis by preventing malignant cells that bind to Clever-1 from being taken up by the lymphatic vessels, and thus to prevent spread of the malignancy into the lymph nodes.

Clever-1 is expressed in lymphatic endothelial cells, certain vascular endothelial cells, but also in a subpopulation of macrophages. On macrophages Clever-1 is known to function as a scavenging receptor, which can mediate endocytic uptake of various molecules such as oxidized-LDL.

Macrophages are traditionally divided into type 1 and type 2 cells. Type 1 macrophages are classical proinflammatory macrophages, which produce large quantities of proinflammatory cytokines and co-stimulatory molecules, and are very efficient in activation of T-cell responses. Type 2 macrophages, in contrast, are immune suppressing cells, which synthesize anti-inflammatory cytokines and induce regulatory T cells and hence profoundly dampen antigen-driven T cell activation. Tumor-associated macrophages are considered harmful as they mature to type 2 macrophages within the tumor environment and suppress anti-tumor immune response (Martinez, F. O. et al. Macrophage activation and polarization. *Front. Biosci.* 13:453-461.) and mediate angiogenic switch, a crucial step in cancer growth (Lin, E. Y., and Pollard, J. W. 2007. Tumor-associated macrophages press the angiogenic switch in breast cancer. *Cancer Res.* 67:5064-5066).

Pregnancy poses a challenge to the immune system, since half of the fetal antigens comes from the paternal origin, which is foreign to the mother. Several immune suppressing mechanisms are known to operate in the placenta to prevent the rejection of the fetus, which can be regarded as a semi-allograft for the maternal immune system. Among the best known examples are expression of non-classical MHC molecules, inhibition of the NK-cell activity, induction of T regulatory cell activity, induction T cell apoptosis and inhibition of complement activation. The suppression of antigen presenting cell activity can also contribute to the induction of tolerance. Among the antigen presenting cells macrophages are prominently present in the placenta.

SUMMARY OF THE INVENTION

We have now identified a new subtype of macrophages in tumors, in the placenta, and also in the blood of pregnant women. This new cell can be defined as a type 2 macrophage cell that also expresses a Clever-1 receptor. We have designated this cell as a "type 3 macrophage". This new "type 3 macrophage" is, like type 2 macrophages, an immune suppressing cell. By modulating (counteracting or stimulating, respectively) the Clever-1 receptor on this new cell, we have surprisingly found that this is a method for affecting the immune system in an individual. Counteracting or down-regulation of the receptor reduces the size of malignant tumor and/or malignant tumor growth. Stimulating or upregulating of the receptor is useful in generation of fetomaternal tolerance and for prevention of pregnancy complications.

Thus, according to one aspect, this invention concerns an isolated cell (type 3 macrophage) which is a type 2 macrophage cell that comprises a Clever-1 receptor, wherein said cell is derived from an individual's tumor or placenta, or from the blood of a pregnant woman.

According to another aspect, the invention concerns a method for affecting the immune system of an individual and for treatment of diseases or conditions related to the function of the immune system, said method comprising modulating the Clever-1 receptor on the novel cell (i.e. the "type 3 macrophage") in said individual.

According to a third aspect, the invention concerns a method for screening of cancer patients that may respond to an anti-Clever-1 therapy, said method comprising
 a) detecting or quantifying of the level of Clever-1 protein in a tumor sample derived from said patient,
 b) comparing the result to a control, and
 c) attributing an increased level of Clever-1 protein in the sample to a responsiveness to said therapy.

According to a fourth aspect, the invention concerns a method for diagnosing of a pregnancy complication or for estimating the risk of such complication in a pregnant woman, said method comprising a) detecting or quantifying the level of Clever-1 protein in a tissue or body fluid from said woman, b) comparing the result to a control, and c) attributing a lack of or a decreased level of Clever-1 protein to a pregnancy complication or a risk therefore.

DETAILED DESCRIPTION OF THE INVENTION

Figure 1A:
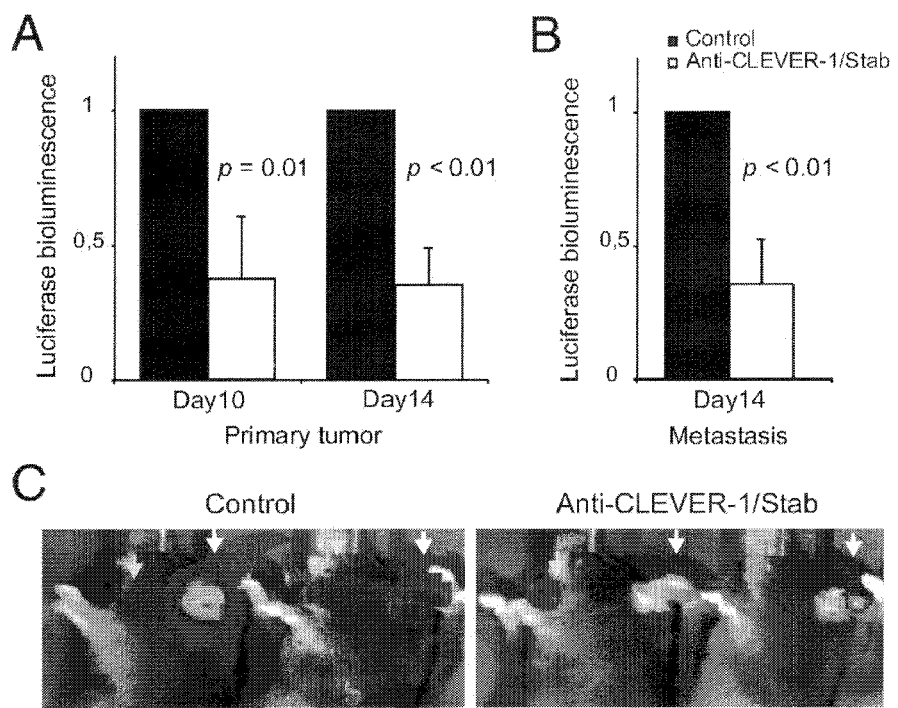
FIG. 1A. Anti-Clever-1 treatment is effective in melanoma. B16-luc melanoma cells were injected subcutaneously into the ear. Growth of the primary tumor and development of metastases were followed by IVIS chemiluminescence detection system. (A) Relative size (mean ±SEM) of the primary tumor after 10 and 14 days in the two treatment groups. (B) Relative size (mean ±SEM) of metastases at the end of the experiment (day 14). The size of the primary tumor and metastases in the control treated group is 1.0 by definition. (C) Examples of animals treated with anti-Clever-1 or control antibody. In the left panel, the second and fourth arrows point to the injection site (primary tumor) and first and third arrows point to the neck metastases. In the right panel, the second and third arrows point to the injection site (primary tumor) and the first arrow points to the neck metastases. Note that one anti-Clever-1 antibody treated mouse does not have a detectable tumor at the site of injection and the other one does not have neck metastases. N=12 in both groups.

Definitions and Preferred Embodiments:

The term "CLEVER-1" is used to denote the protein disclosed in WO 03/057130, Common Lymphatic Endothelial and Vascular Endothelial Receptor-1, a binding protein that mediates adhesion of lymphocytes (and malignant tumor cells) to endothelium in both the systemic vasculature and in the lymphatics. The nucleotide sequence (7879 nt) and amino acid sequence of Clever-1 is shown in SEQ ID NO. 1. In the nucleotide sequence of Clever-1 there are four nucleotide differences compared to Genebank entry AJ 275213 (stabilin-1), i.e., nucleotides 1131, 2767, 6629 and 6969.

The term "type 2 macrophage" shall be understood as an immune suppressing macrophage which expresses a mannose receptor.

The term "type 3 macrophage" shall be understood as a subpopulation of type 2 macrophages that in addition to the mannose receptor also expresses the Clever-1 receptor. The Clever-1 receptor on the type 3 macrophage cell can be either the entire sequence (SEQ ID NO. 1), a slight modification thereof (such as Stabilin-1) or a fragment thereof.

The term "treatment" or "treating" shall be understood to include complete curing of a disease or disorder, as well as amelioration or alleviation of said disease or disorder.

The term "prevention" shall be understood to include complete prevention, prophylaxis, as well as lowering the individual's risk of falling ill with said disease or disorder.

The term "individual" refers to a human or animal subject.

The term "effective amount" is meant to include any amount of an agent according to the present invention that is sufficient to bring about a desired therapeutic result, especially upon administration to an animal or human subject.

The term "inhibiting" or "inhibition" shall be understood to include not only complete inhibition but also any grade of suppression.

In one embodiment, the method for affecting the immune system of an individual by modulating of the Clever-1 receptor on the type 3 macrophage cell can be used for reducing the size of malignant tumor and/or by reducing malignant tumor growth in an individual. In this embodiment, an effective amount of an agent capable of counteracting the influence of or for down-regulating the expression of the Clever-1 protein is administered to the individual.

In another embodiment, the method for affecting the immune system of an individual by modulating of the Clever-1 receptor on the type 3 macrophage cell can be used for maintaining feto-maternal tolerance and/or prevention of a pregnancy complication in a pregnant woman. In this embodiment, to the pregnant woman is administered either i) an effective amount of an agent, which up regulates the expression of the Clever-1 protein or which stimulates said protein, or ii) in vitro cultivated type 3 macrophage cells.

Preferred Agents

The term "an agent capable of counteracting the influence of Clever-1" shall be understood to include peptides or proteins (such as soluble Clever-1 or Clever-1 antagonist antibodies) blocking the Clever-1 protein as well as any inhibitors, particularly small molecule inhibitors, useful to inhibit the protein activity. Particularly useful agents are antibodies.

The term "an agent capable of down-regulating the expression of Clever-1" shall be understood to include antisense oligonucleotides, small interfering RNAs (siRNA) as well as ribozymes, or vectors being capable of expressing them, or essential parts thereof, in vivo.

The term "antibody" is used in the broadest sense and specifically covers single monoclonal antibodies (including agonist and antagonist antibodies), polyclonal antibodies, as well as antibody fragments and single chain antibodies (e.g., Fab, F(ab')$_2$, Fv), so long as they exhibit the desired biological activity. Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen. Single chain "Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site. See, Ladner et al., U.S. Pat. No. 4,946,778, and Bird, R. E. et al., *Science,* 242:423-426 (1988).

The term "antibody" shall be understood to include also chimeric, humanized or primatized (CDR-grafted) antibodies, as well as chimeric or CDR-grafted single chain antibodies, and the like, comprising portions derived from different species. "Chimeric" antibodies (immunoglobulins) have a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., U.S. Pat. No. 4,816,567; Morrison et al., *Proc. Natl. Acad. Sci. USA* 81:6851-6855 (1984). The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567. See also, Newman, R. et al., *BioTechnology* 10: 1455-1460 (1992), regarding primatized antibody.

Particularly preferred Clever-1 antagonist antibodies are the monoclonal antibodies 3-266 (DSM ACC2519) and 3-372 (DSM ACC2590), both deposited under the terms of the Budapest Treaty on the International Recognition of the Deposit of Micro-organisms for the Purposes of Patent Procedure on Aug. 21, 2001, with DSMZ-Deutsche Sammlung von Mikroorganismen and Zellkulturen GmbH, Mascheroder Weg 1b, D-38124 Braunschweig. See WO 03/057130.

For treatment of human individuals, humanized or chimeric or primatized variants of the monoclonal antibodies mentioned above are preferred.

Preferable inhibitors are small molecule inhibitors.

Preferably, the agent capable of down-regulating the expression of Clever-1, is a small interfering RNAs (siRNA) or an expression vector comprising nucleic acid encoding the siRNA duplex or the antisense strand of the duplex in a manner which allows expression of the siRNA duplex or antisense strand within a mammalian cell. Such siRNA duplexes for another protein, VAP-1, are described in WO 2006/134203.

The principle of siRNA is extensively presented in literature. As examples can be mentioned the US patent publications 2003/0143732, 2003/0148507, 2003/0175950, 2003/0190635, 2004/0019001, 2005/0008617 and 2005/0043266. An siRNA duplex molecule comprises an antisense region and a sense strand wherein said antisense strand comprises sequence complementary to a target region in an mRNA sequence encoding a certain protein, and the sense strand comprises sequence complementary to the said antisense strand. Thus, the siRNA duplex molecule is assembled from two nucleic acid fragments wherein one fragment comprises the antisense strand and the second fragment comprises the sense strand of said siRNA molecule. The sense strand and antisense strand can be covalently connected via a linker molecule, which can be a polynucleotide linker or a non-nucleotide linker. The length of the antisense and sense strands are typically about 19 to 21 nucleotides each. Typically, the antisense strand and the sense strand both comprise a 3'-terminal overhang of a few, typically 2 nucleotides. The 5'-terminal of the antisense is typically a phosphate group (P). The siRNA duplexes having terminal phosphate groups (P) are easier to administrate into the cell than a single stranded antisense. In the cell, an active siRNA antisense strand is formed and it recognizes a target region of the target mRNA. This in turn leads to cleaving of the target RNA by the RISC endonuclease complex (RISC =RNA-induced silencing complex) and also in the synthesis of additional RNA by RNA dependent RNA polymerase (RdRP), which can activate DICER and result in additional siRNA duplex molecules, thereby amplifying the response.

The term "complementary" means that the nucleotide sequence can form hydrogen bonds with the target RNA sequence by Watson-Crick or other base-pair interactions. The term shall be understood to cover also sequences which are not 100% complementary. It is believed that also lower complementarity might work. However, 100% complementarity is preferred.

The siRNA shall, when used as a pharmaceutical, be introduced in a target cell. The delivery can be accomplished in two principally different ways: 1) exogenous delivery of the oligonucleotide or 2) endogenous transcription of a DNA sequence encoding the oligonucleotide, where the DNA sequence is located in a vector.

Normal, unmodified RNA has low stability under physiological conditions because of its degradation by ribonuclease enzymes present in the living cell. If the oligonucleotide shall be administered exogenously, it is highly desirable to modify the molecule according to known methods so as to enhance its stability against chemical and enzymatic degradation.

Modifications of nucleotides to be administered exogenously in vivo are extensively described in the art. Principally, any part of the nucleotide, i.e the ribose sugar, the base and/or internucleotidic phosphodiester strands can be modified.

It should be stressed that the modifications mentioned above are only non-limiting examples.

A useful target region can easily be identified by using any of the numerous academic or commercially affiliated algorithms that have been developed to assist scientists to locate utilizable siRNA sequences. As examples of such software systems can be mentioned siDirect http_colon_//_design_dot_RNAi_dot_jp (Nucleic Acids Res. 2004 Jul. 1; 32: W124-9); TROD (T7 RNAi Oligo Designer http_colon //_www_dot_cellbio_dot_unige_dot_ch_/_RNAi_dot_html; Nucleic Acids Res. 2004 Jul. 1; 32: W121-3); DEQOR (http_colon_//_cluster-1dot_mpi-cbg_dot de/Deqor/deqor_dot_html; Nucleic Acids Res. 2004 Jul. 1; 32: W113-20) or programs available at http_colon_//_www_dot_genscript_dot_com, http_colon_//_www_dot_genscript_dot_com/rnai_dot_html#design or http_colon_//_www_dot_genscript_dot_com/sirna_ca dot_html#design; Bioinformatics 2004 Jul. 22; 20(11)1818-20. An essential criterion of the tools is to achieve siRNAs with maximum target-specificity for mammalian RNA interference where off-target gene silencing is avoided. The usefulness of any sequence identified by such algorithms should thereafter be verified by experiments.

Preferred agents for stimulating the Clever-1 protein are, for example agonist antibodies and small molecule agonists. By "agonist antibody" is meant an antibody which is able to bind to Clever-1 and facilitate adhesion of other tissue.

Preferred small molecule agonists are immune suppressing agents, such as an anti-inflammatory agents, especially interleukins such as, interleukin-4, interleukin -13 or steroid hormones such as dexamethasone, or a combination thereof.

For maintaining feto-maternal tolerance and/or prevention of a pregnancy complication in a pregnant woman, also administration of the type 3 macrophages having been cultivated in vitro, is possible.

Diseases Responding to the Treatment

The method for treating or preventing cancer by reducing the size of malignant tumor and/or by reducing malignant tumor growth according to this invention is applicable to all forms of cancers. Thus, any benign or malignant tumor or metastasis of malignant tumor, such as skin cancer and colon cancer can be treated. Also leukemias, lymphomas and multiple myelomas can be treated. Particularly, melanomas and lymphomas respond very well to the treatment.

We believe that the method according to this invention is useful in the treatment or prevention of all kinds of sarcomas, for example fibrosarcoma, liposarcoma, chondrosarcoma, osteosarcoma, angiosarcoma, lymphangisarcoma, leiomyosarcoma, and rhabdomyosarcoma, mesothelioma, meningoma, leukemias, lymphomas, as well as all kinds of carcinomas, such as squamous cell carcinomas, basal cell carcinoma, adenocarcinomas, papillary carcinomas, cystadenocarcinomas, bronchogenic carcinomas, melanomas, renal cell carcinomas, hepatocellular carcinoma, transitional cell carcinomas, choriocarcinomas, seminomas, and embryonal carcinomas.

By stimulating of Clever-1, it is possible to main feto-maternal tolerance and/or prevent pregnancy complications in a pregnant woman. Pregnancy complications that can be treated are especially risk of spontaneous abortion and pre-eclampsia.

Administration Routes, Formulations and Required Dose

The pharmaceutical compositions to be used in the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, ocular routes or via inhalation. Alternatively, administration can be by the oral route. Particularly preferred for small molecule inhibitors may be oral administration. In addition to the pharmacologically active compounds, the pharmaceutical preparations of the compounds preferably contain suitable pharmaceutically acceptable carriers comprising excipients and auxiliaries that facilitate processing of the active compounds into preparations that can be used pharmaceutically.

For reducing the size of malignant tumor and/or by reducing malignant tumor growth, intra-tumoral administration may be useful.

For maintaining feto-maternal tolerance and/or prevention of a pregnancy complication in a pregnant woman, intra-placental administration of the effective agent may also be useful.

The siRNA duplex for use in this invention can be administered to the individual by various methods. According to one method, the siRNA may be administered exogenously as such, or in the form of a pharmaceutical composition admixed with a suitable carrier which may be, for example, a liposome, cholesterol, lithocholic acid, lauric acid, a cationic lipid, polyethylenimine (PEI) or its conjugates with polyethylene glycol (PEG) derivatives. However, also other carriers can be used.

The siRNA can be administered systemically or locally. As suitable routes of administration can be mentioned intravenous, intramuscular, subcutaneous injection, inhalation, oral, topical, ocular, sublingual, nasal, rectal, intraperitoneal delivery and transdermal delivery systems. The composition containing the siRNA can, instead of using direct injection, also be administered by use of, for example, a catheter, infusion pump or stent.

Another method to achieve high concentrations of the siRNA in cells is to incorporate the siRNA-encoding sequence into an expression vector and to administer such a vector to the individual. In this application, the expression vector could be construed so that either the siRNA duplex or only the antisense strand thereof is expressed, e.g. in the form of short hairpin RNAs. The expression vector can be a DNA sequence, such as a DNA plasmid capable of eukaryotic expression, or a viral vector. Such a viral vector is preferably based on an adenovirus, an alphavirus, an adeno-associated virus or a retrovirus. Preferably, the vector is delivered to the patient in similar manner as the siRNA described above. The delivery of the expression vector can be systemic, such as intravenous, intramuscular or intraperitoneal administration, or local delivery to target tissue or to cells explanted from the patient, followed by reintroduction into the patient.

Since intravenous administration of siRNA preferentially targets liver vasculature (Lewis D L and Wolff J A, Methods Enzymol. 2005; 392:336-50; Soutschek J et al., Nature. 2004 Nov. 11; 432(7014):173-8; and Song E et al., Nat Med. 2003 March; 9(3):347-51), diseases of liver are especially suitable targets for intervention. Especially siRNA:s embedded in liposomes have been reported to be very useful for targeting liver tissue. No toxic side-effects have been reported.

Thus, a typical dose is in the dosage range of about 0.1 microgram/kg to about 300 mg/kg, preferably between 1.0 microgram/kg to 10 mg/kg body weight. Compounds for use in the present invention may be administered in a single daily dose, or the total daily dosage may be administered in divided doses of two, three or four times daily. When siRNA is used, a typical daily dose is in the dosage range of about 1 mg/kg to about 20 mg/kg, preferably about 5 mg/kg body weight. The suitable administration frequence is believed to be 1 to 2 doses daily. When the RNAi is delivered by an expression vector, a single dose (or a single doses repeated at certain intervals, e.g. once in week) is believed to be enough.

Diagnostic Methods:

The method for detection or quantification of Clever-1 may be based on detecting or quantifying the level of the Clever-1 protein in a tissue or body fluid by i) determining the Clever-1 mRNA expression from said tissue or body fluid by RT-PCR, or by a hybridizing technique, or ii) subjecting the tissue or body fluid expected to contain the Clever-1 protein to an binder (such as antibody, affibody or aptamer) recognizing said Clever-1, and detecting and/or quantifying said binder, or subjecting said tissue or body fluid to analysis by proteomics technique.

The hybridizing technique include, for example DNA hybridization and northern blot. The detection or quantification of the antibody or other binder can be performed according to standard immunoassay protocols, such as label-linked immunosorbent assays, western blot and immunohistochemical methods The invention will be illuminated by the following non-restrictive Experimental Section.

Experimental Section

Materials and Methods

Animals. Balb/C and C57B16 mice (6-9 weeks old) and New Zealand white (NZW) rabbits were used in the in vivo experiments. The Local Ethical Committee approved the experimental procedures that were used in this study.

Tumor cell lines. KCA, a human lymphoblastoid cell line was a kind gift from E. Engleman (Stanford University, CA). B16-F10-luc-G5 melanoma cell line containing a luciferase construct was purchased from Xenogen (Alameda, Calif.). Tumor cells were cultured in RPMI 1640 (KCA) and MEM/HBSS (B16 melanoma) (HyClone, Logan, Utah) supplemented with 10% FBS (Invitrogen, Gibco), non-essential amino acids (Biologial Industries, Haemek, Israel), 200mM L-glutamine (B10 Whittaker, Walkersville, Md.), 1mM Sodium pyruvate (Invitrogen, Gibco), and MEM Vitamin solution (Invitrogen, Gibco, Paisley, UK).

Tumor cell migration via lymphatics in rabbits. Rabbits were given 3-372 (anti-Clever-1, n=8) or control antibody (n=9) 2 mg/kg i.v. one day before and on the same day as the lymphoma cell transfer. In addition 0.5 mg of antibodies were added to the CFSE-labeled KCA lymphoma cell suspension that was given subcutaneously into the footpads. After 24 hours from the cell transfer, popliteal lymph nodes were collected and cell suspensions were analysed by flow cytometry.

Lymphatic metastasis model. B16-F10-luc-G5 melanoma cells at a dose of 400,000 cells in 30 µl of RPMI 1640 (GIBCO) were injected subcutaneously into the left ear of mice. Inoculated tumors can be seen as black nodules through the skin. Tumor growth was measured by luciferase bioluminescence (Marttila-Ichihara, F. et al., *Blood* 112:64-72) twice a week. In brief, mice were anesthetized with 2.5% isoflurane (Becton Dickinson). One hundred fifty mg/kg of substrate D-luciferin sodium salt (Synchem, Kassel, Germany) was injected intraperitoneally to mice 10 min before imaging. A black and white photographic image was taken in the black chamber with a cooled (−70 C) CCD camera (IVIS; Xenogen, Alameda, Calif.). Signal intensity was quantified as the photon counts using the Living Image software (Xenogen). One day before tumor injection, twelve C57B1/6J mice were treated with anti-Clever-1(Schledzewski, K. et al. *J. Pathol.* 209:67-77) antibody and the same number of mice were treated with NS-1 control antibody with subcutaneous injection of the antibodies at a dose of 50 μg into the ear. Intraperitoneal antibody administration at a dose of 100 μg was started one day after tumor injection and then repeated every third day. Mice were sacrificed on day 14.

Immunohistochemistry. Acetone fixed frozen sections of the ear and peripheral lymph node metastases of the mice were stained with rat mAb against macrophage mannose receptor (MR, MR5D3, a marker for type 2 macrophages, kind gift from L. Martinez-Pomares), PV-1 antigen (blood vessel antigen, MECA-32, kind gift from E. Butcher, Stanford University, CA), CD31 (a marker of both blood and lymphatic vessels; BD Pharmingen), CD3 (BD Pharmingen), CD8 (Caltag) or with a negative control mAb (Hermes-1 against human CD44). FITC-conjugated anti-rat Ig (Sigma) diluted in PBS containing 5% normal mouse serum was used as the second stage antibody. Tumor tissues, metastases and lymph node sections were also stained using biotinylated anti-Clever-1 followed by Streptavidin-Alexa Fluor 546. For Foxp3 expression, frozen sections were fixed with 2% paraformaldehyde, stained with anti-Foxp3 (eBioscience) followed by peroxidase-conjugated rabbit anti-rat Ig (Dako, Denmark). 3,3'-diaminobenzidine hydrochloride in PBS containing 0.03% hydrogen peroxide was used as a chromogen and the sections were counterstained with hematoxylin. The sections were analyzed using Olympus BX60 microscope and cell^D version 2.6 software (Soft Imaging Solutions GmbH). SPARC stainings were analyzed using Image J software.

Immunizations. Rabbits were immunized to the footpads with a cocktail (volume 200 μl) containing heat killed *Salmonella enteritidis*, *E. coli* LPS (10 mg) and bovine serum albumin (1 mg). At the same time the rabbits received either anti-Clever-1 antibody (3-372, n=5) or class matched negative control antibody (NS-1, n=5) 2 mg/kg. Non-immunized rabbits were used as controls. The antibody treatments were repeated on day 2, 4, 7 and 9 Immunization was repeated on day 7. Serum samples were collected on day 7 and 11 and antibody titers were analyzed by ELISA. Briefly, polystyrene microtiter plates (Nunc, Roskilde, Denmark) were coated with pretested concentrations of *E. coli* LPS (Difco Laboratories, Detroit, USA), SDS-extract of *Salmonella enteritidis* and BSA (fraction V, ICN Biomedicals, Inc. Ohio, USA). After incubation with serum samples IgM and IgG antibodies in the wells were detected with alkaline-phosphatase-conjugated anti-rabbit IgM (Southern Biotechnology Associates, Birmingham, Ala., USA) and anti-rabbit IgG (Dako Patts A/S, Copenhagen, Denmark). The absorbances were detected with a Victor multilabel counter (Wallac, Turku, Finland) at a wavelength of 405 nm.

Mice were immunized with subcutaneous injection of 50 μg ovalbumin (OVA, grade V; Sigma, St Louis, Mo.) in incomplete Freund's adjuvant into the footpads Immunizations were repeated three times (on day 0, 7 and 14). Mice were treated one hour before first immunization with subcutaneous injection of anti-Clever-1 or control antibody (NS-1), 50 μg/mouse, n=6+6) and intraperitoneally three times a week (100 μg/mouse). Mice were sacrificed on day 17 and popliteal lymph nodes, inguinal lymph nodes and spleens were collected and cells were isolated for flow cytometric analyses and for proliferation assay. Spleens were homogenized and red cells were lysed using hypotonic saline. T cells ($0.2 \times 10^6$) were co-cultured with increasing concentration (0-2 mg/ml) of OVA in round-bottom 96-well plates. Co-cultures were incubated in HEC-medium for 3 d and pulsed with $^3$H-thymidine (1 μCi [0.037 MBq] per well) for the final 6 h. Cells were harvested using semi-automated plate harvester (Tomtech MACH III; Fisher Scientific, Hampton, N.H.) and counted with the 1450 Microbeta counter (Wallac). The antibody titers against OVA were determined by ELISA as described (Stolen, C. M. et al., *Immunity* 22:105-115). The phenotype analyses were carried out as explained above. In addition, FoxP3 positive regulatory T cells were detected using a kit from eBioscience according to the manufacturer's instructions.

Results

Figure 1B:
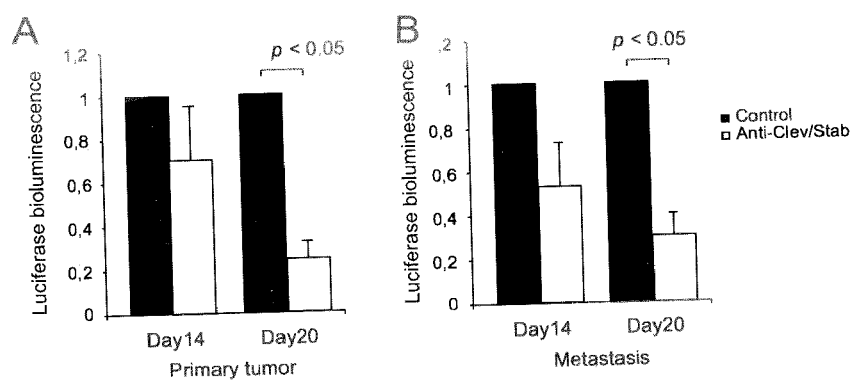
FIG. 1B. The figure shows the development of primary tumor (A) and metastases (B) when the antibody treatment was started three days after the injection of B16 melanoma cells (day 14, n=12 in both groups and day 20, n=6 in both groups).

Antitumor Effect:

Under Clever-1 treatment both primary tumor and metastases of melanoma remain small. To study, whether targeting Clever-1 can have beneficial effects on tumor development we utilized B16 melanoma model in mouse. Both the primary tumors in the ear and the metastases in the draining lymph nodes in the neck reached only about 30% of the size when treated with anti-Clever-1 antibody in comparison to the control treated animals (FIG. 1A, A-C). Because in clinical settings the treatments are started after the malignant growth has been diagnosed, we also made sets of experiments better mimicking the clinical situation. In these experiments, we let the tumors grow three days before starting the antibody therapy and completed the experiment either on day 14 or 20 after the tumor cell injections. Also in these experimental set ups the antibody therapy was effective leading to statistically significant reduction in primary tumors and metastases on day 20 (FIGS. 1B, A and B).

Figure 2:
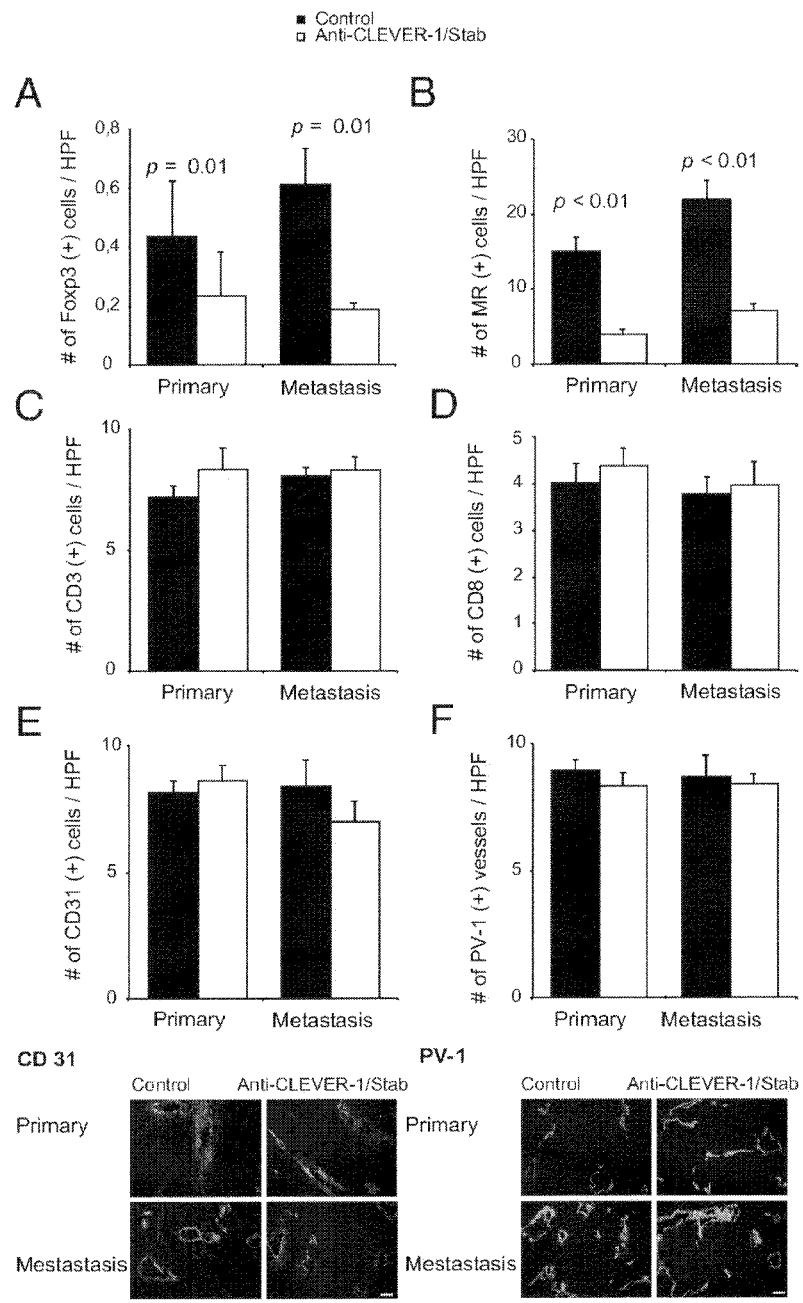
FIG. 2. Anti-Clever-1 treatment reduces number of type 2 macrophages and regulatory T cells in tumors but does not affect the vasculature. (A) Number of regulatory T cells. (B) Number of type 2 macrophages. (C) Number of CD3 positive T cells. (D) Number of CD8 positive T cells. (E) Number of CD31 positive vessels and examples of immunofluoresecnce staining of primary tumors and metastases with anti-CD31 antibody of anti-Clever-1 treated and control antibody treated mice. (F) Number of PV-1 positive vessels detected with anti-MECA-32 antibody and examples of immunofluoresecnce staining of primary tumors and metastases with anti-MECA-32 antibody of anti-Clever-1 treated and control antibody treated mice. HPF (high power field). Bar 100 µm.

Anti-Clever-1 treatment reduces number of type 2 macrophages and regulatory T cells but is not anti-angiogenic Inhibition of melanoma cell migration via afferent lymphatics into the draining lymph nodes could explain the reduced size of the metastases subsequent to antibody therapy. However, it cannot give explanation for the small size of the primary tumors. Therefore we analyzed the number of different subpopulations of tumor infiltrating leukocytes and vessels. The number of tumor infiltrating leukocytes could reflect the efficacy of anti-tumor immune response and the number of vessels the angiogenic activity that controls tumor growth (Dirkx, A. E. e al. *J. Leukoc. Biol.* 80:1183-1196). The latter aspect is also relevant regarding Clever-1 itself, because it has been reported to contribute to angiogenesis in vitro (Adachi, H., and Tsujimoto, M. 2002. *J. Biol. Chem.* 277:34264-34270). The number of type 2 macrophages and regulatory T cells was greatly diminished both in primary tumors and metastases (FIGS. 2A and 2B). This reduction was selective as the number of CD3 and CD8 positive cells were comparable in both treatment groups (FIGS. 2C and 2D). The number of blood and lymphatic vessels (CD31 and/or PV-1 positive) and their density was the same after anti-Clever-1 and control antibody therapy (FIGS. 2E and 2F). Thus, the number of the regulatory immune cell types is diminished subsequent to targeting Clever-1 but both the blood and lymphatic vasculature seem to remain intact.

Type2 macrophages in melanoma are Clever-1 positive and antibody therapy does not completely eliminate them. A possible explanation for the diminished number of type 2 macrophages subsequent to anti-Clever-1 treatment is that the treatment kills the Clever-1 positive macrophages by complement mediated killing. However, this is not the case as 50.3±16.9% of type 2 macrophages in anti-Clever-1 and 65.9±16.7% of control antibody treated tumors are Clever-1 positive in primary tumors (FIG. 3A), although their absolutely numbers are greatly diminished due to the antibody treatment (FIG. 2B). In this context, however, it should be noted that Clever-1 positive macrophages were smaller and dimmer after anti-Clever-1 treatment than after control treatment.

Figure 3:
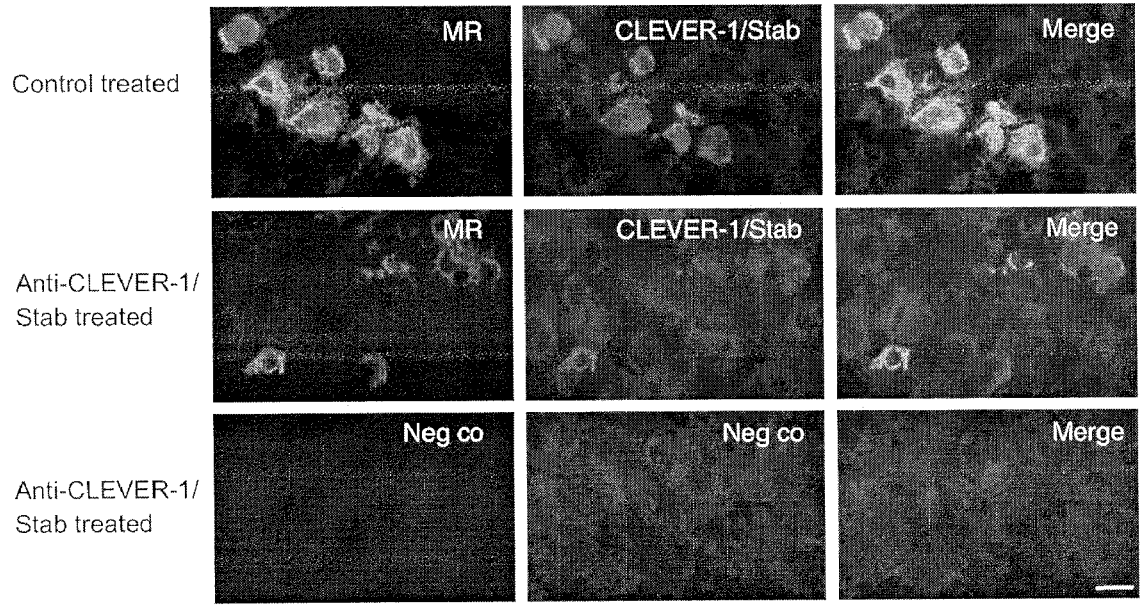
FIG. 3. Tumor associated type 2 macrophages express Clever-1 but they are absent in lymph nodes subsequent to immunization. (A) Immunofluorescence staining of melanoma metastases of anti-Clever-1 and control treated mice. Double staining with anti-MR shown in left panels and anti-Clever-1 shown in center panels. (B) Immunohistochemical stainings of macrophages in popliteal lymph nodes after immunization with OVA. MR shown in left panels, Clever-1 shown in center panels. (C) Staining of lymphatic endothelium of the same popliteal lymph nodes after OVA immunization. MR shown in left panels, Clever-1 shown in center panels. Bars, (A) and (B) 50 µm, (C) 100 µm.
Figure 3:
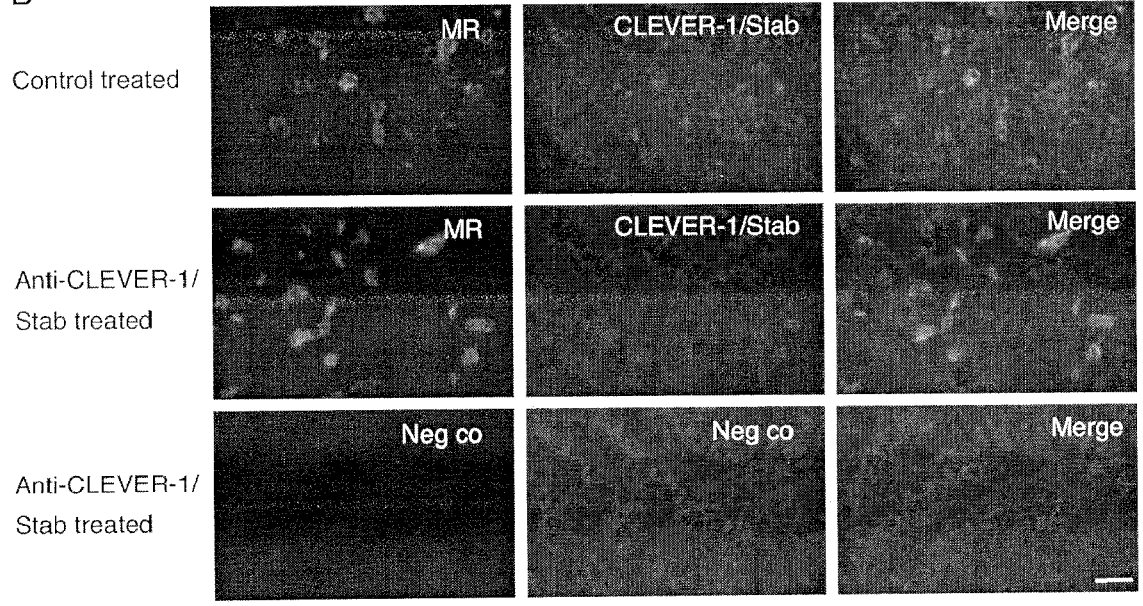
Figure 3:
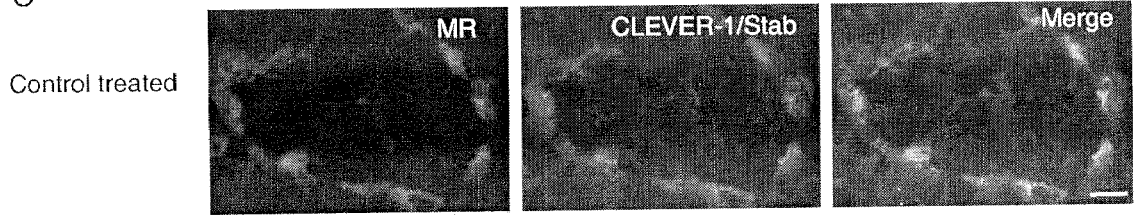
Figure 4:
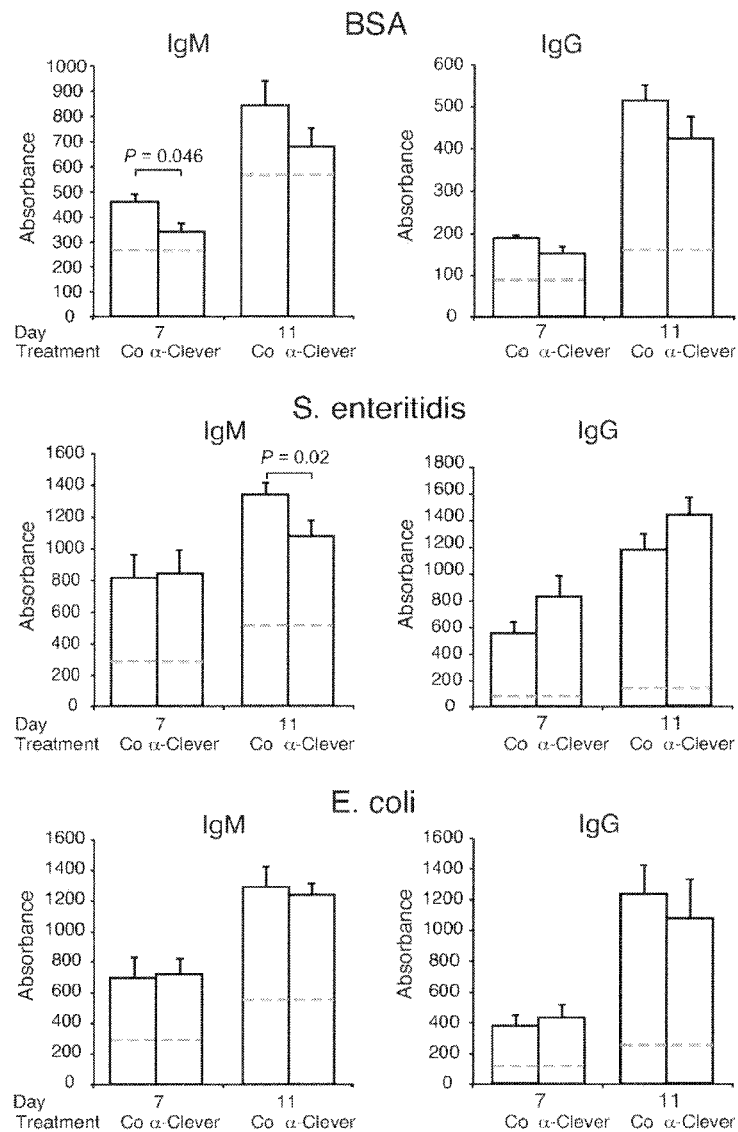
FIG. 4. Anti-Clever-1 treatment does not significantly impair the antibody response. Rabbits were immunized with BSA, heat killed *Salmonella enteritidis* and *E. coli* LPS and treated either with anti-Clever-1 or control antibody. The antibody titers were measured on days 7 and 11 after primary immunization using ELISA. The dashed line indicates the titers in non-immunized animals (receiving the antibody).
Figure 5:
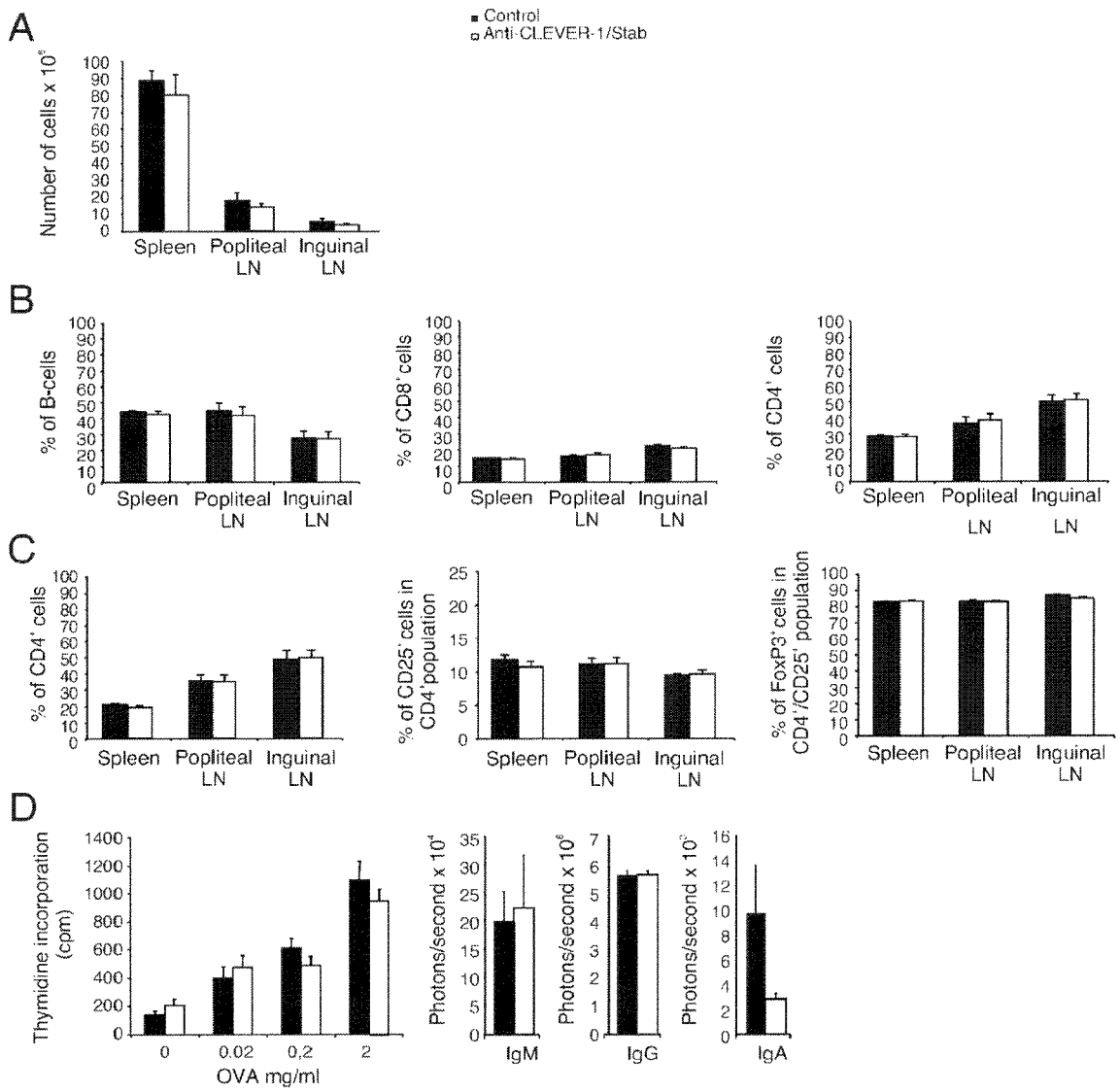
FIG. 5. Anti-Clever-1 treated mice respond normally to OVA immunization. (A) Number of lymphocytes in the indicated organs. (B) Percentages of B cells, CD4 and CD8 positive T cells. (C) Percentages of regulatory T cells. (D) Proliferation responses and antibody titers to OVA.

Antibody therapy does not significantly impair normal immune response. Since the Clever-1 blockade significantly prevents lymphocyte and tumor cell migration into the draining lymph nodes, it may also affect the normal immune response. We tested this possibility both in the rabbit and mouse models. Rabbits were treated either with anti-Clever-1 or a control antibody and immunized into the footpad with BSA, *Salmonella enteritidis* and *E. coli* LPS (FIG. 4). No statistically significant differences were detected in antibody responses of IgM and IgG classes. The only exceptions were slight decreases in the IgM response at day 7 in BSA and day 11 in *Salmonella enteritidis* in the rabbits treated with anti-Clever-1 antibody. Mice were immunized into the footpads with OVA. Absolute lymphocyte numbers and percentages of different subpopulations in lymph nodes and spleen of both treatment groups were comparable (FIGS. 5A-C) as well as the OVA-specific T and B cell responses (FIG. 5D). In contrast to MR positive type 2 macrophages within the melanoma, the MR positive macrophages were Clever-1 negative in popliteal lymph nodes of the normal and immunized mice while the lymphatic endothelium was Clever-1 positive (FIGS. 3B and 3C). Also the MR positive macrophages within the lymph nodes were markedly smaller than in the tumors suggesting that MR$^+$/Clever-1$^+$ macrophages within the tumor is a unique subtype.

Figure 10:
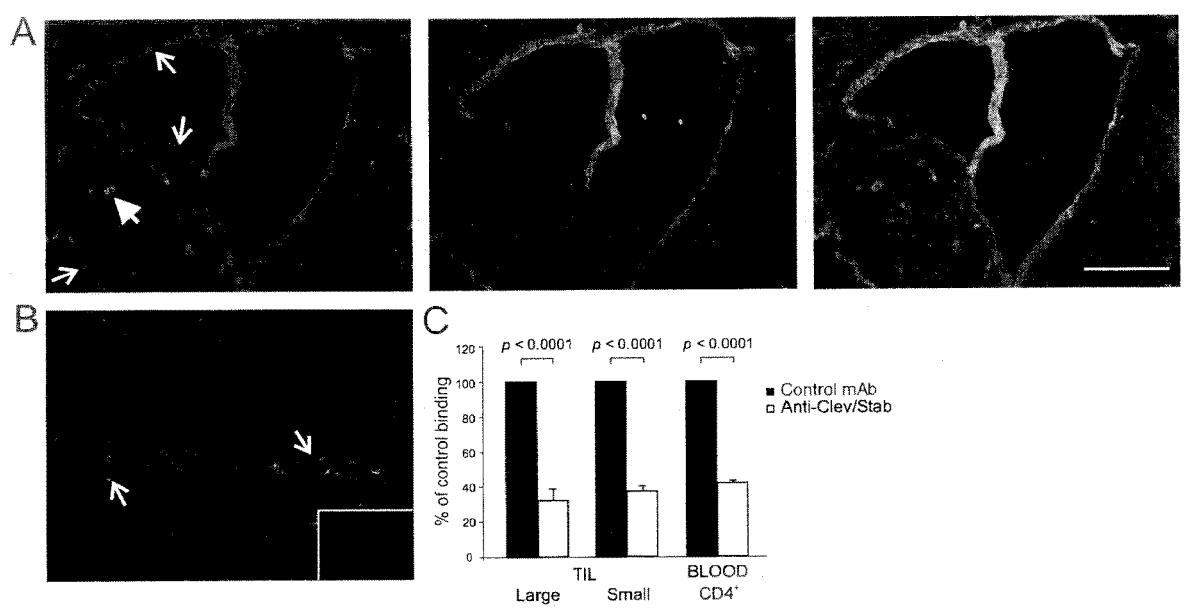
FIG. 10. Expression of Clever-1/Stabilin-1 is induced on tumor vasculature in melanoma, where it binds tumor infiltrating leukocytes and peripheral blood CD4 positive cells. (A) Two-color staining of Clever-1/Stabilin-1 with biotinylated 1.26 antibody (left panel) and PV-1 with MECA-32 antibody (middle panel) identifying the tumor vessels. A merger of the stainings with 1.26 and Meca-32 is shown on the right panel. The vessels are pointed out by thin arrows in the left panel and a type 2 macrophage (positive for Clever-1/Stabilin-1) is pointed out by a thick arrow in the left panel. Bar 100 µm (B) Vascular positivity was confirmed with another monoclonal antibody (9-11) against Clever-1/Stabilin-1 (N-terminal 3 kb fragment). Staining with a negative control antibody is shown in the inset. (C) Clever-1/Stabilin-1 on vasculature mediates binding of tumor infiltrating leukocytes. Binding of large and small tumor infiltrating leukocytes (TIL) as well as CD4 positive cells from the blood to vessels in melanomas obtained from mice treated in vivo with anti-Clever-1/Stabilin-1 (n=3) or control antibody (n=3) was analyzed using ex vivo frozen section assays. The results are presented as mean %±SEM of binding obtained from melanomas of mice treated with the control antibody (by definition 100%).

To find a mechanism behind the reduced number of type 2 macrophages in the tumors we tested, whether the entrance of them or their precursors becomes inhibited during the antibody therapy. First, we analyzed Clever-1/Stablin-1 expression on tumor vasculature. Majority of the vessels within the tumor are enlarged with widely open lumen and unlike normal flat walled vessels they express Clever-1/Stabilin-1. This expression was confirmed using two different antibodies against Clever-1/Stabilin-1 (FIGS. 10, A and B). Next, we collected tumors from both anti-Clever-1/Stabilin-1 and control antibody treated animals and tested binding of tumor infiltrating leukocytes and peripheral blood CD4 positive T cells to vessels in those tumors ex vivo. Both tumor infiltrating large leukocytes consisting from macrophages and myeloid cells and tumor infiltrating small lymphocytes bound poorly to tumor vessels of Clever-1/Stabilin-1 treated animals. Also adhesion of CD4 positive blood lymphocytes was reduced (FIG. 10C). These findings show that Clever-1 blocking therapy prevents monocytes/macrophages and lymphocytes from binding to the vascular system of the tumor. As a result, the development of type 3 macrophages is reduced. Without Clever-1 blocking, type 3 macrophages originating from monocytes entering from the blood stream, will develop and differentiate in the tumor tissue.

Figure 6:
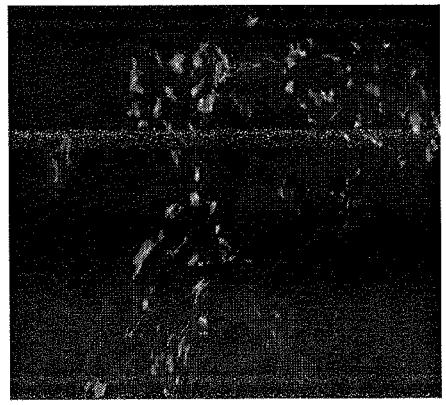
FIG. 6. Expression of Clever-1 in placenta. Frozen sections placenta were stained with anti-Clever-1 antibody (3-372), anti-CD14 (as a macrophage marker) and with negative control antibodies followed appropriate second stage reagents.
Figure 6:
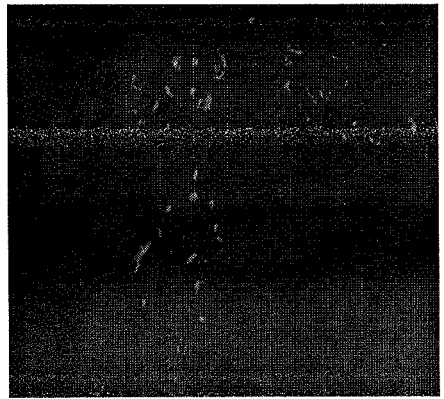
Figure 6:
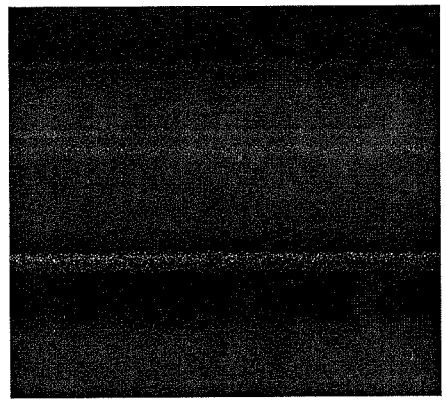
Figure 6:
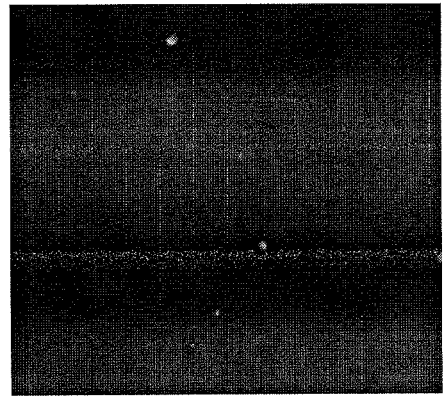

Fetomaternal Tolerance:

Expression of Clever-1 in placenta. When normal placentas (at term) were immunohistochemically stained for Clever-1, many brightly positive leukocytes were found (FIG. 6). Multicolor FACS analyses further showed that placental NK cells were Clever-1 negative, whereas most CD14 positive macrophages expressed Clever-1 (data not shown).

Figure 7:
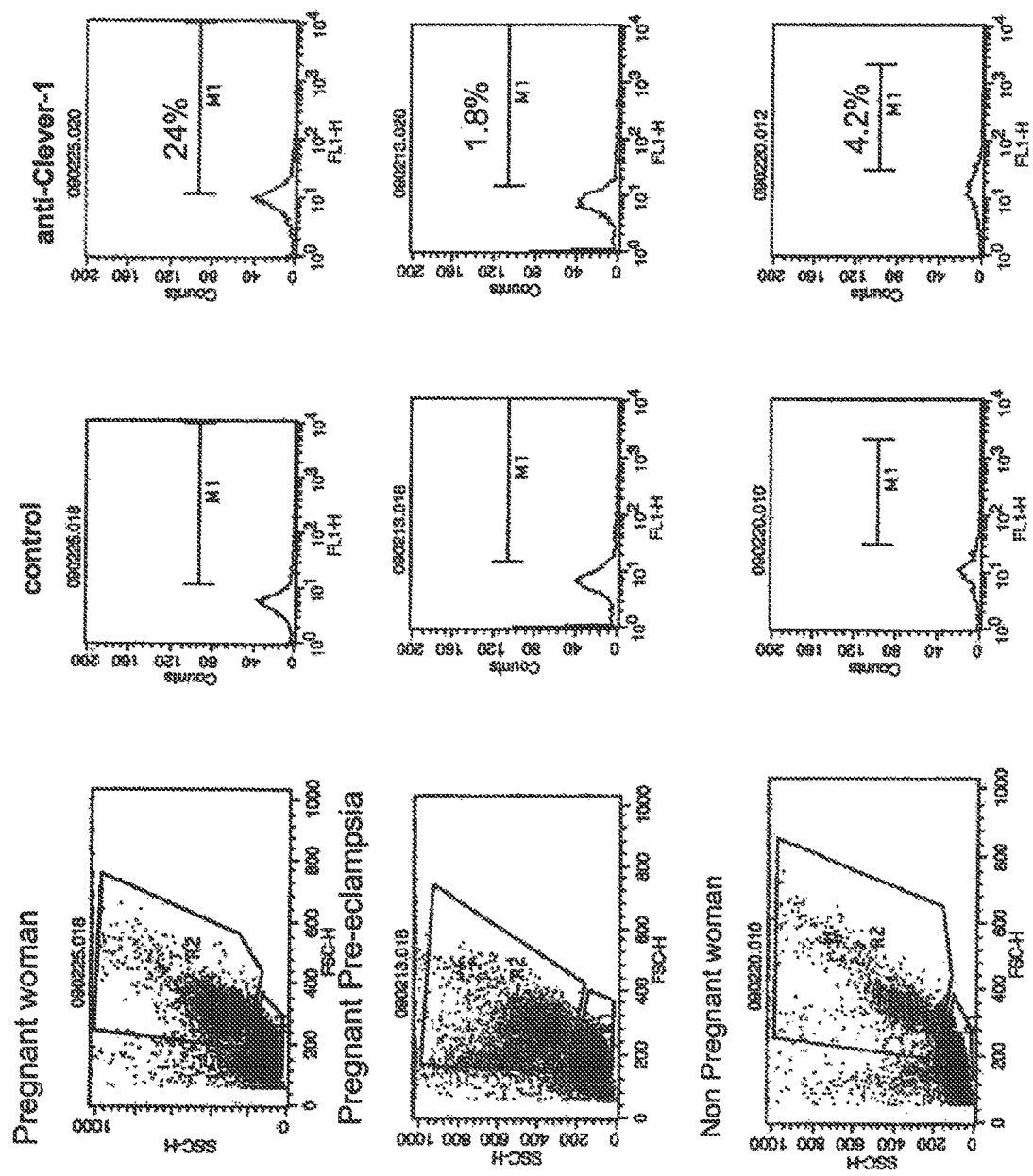
FIG. 7. Cell-surface expression of Clever-1 in blood monocytes during normal pregnancy. Peripheral blood mononuclear cells were isolated from normal, non-pregnant volunteers, from normal pregnant women and from a pregnant women with a mild pre-eclampsia. The mononuclear cells were separated using Ficoll gradient centrifugations and stained with anti-Clever-1 and the control antibody (both at 10 µg/ml), and FITC-conjugated anti-mouse Ig. The cells were analyzed using FACS. The cell populations (R2) analyzed are shown on the left panels with forward and side scatters. In the histograms the fluorescence intensity is in a logarithmic scale on the x axis and relative number of cells on y axis. The percentages shown on the right panels are obtained by deducting the percentage of the positive cells stained with the negative control antibody (=background).

Expression of Clever-1 in blood. Clever-1 was practically absent or expression was very low on the surface of blood mononuclear leukocytes in healthy individuals tested (FIG. 7). In contrast, pregnant women had clearly detectable levels of Clever-1 on the surface of blood monocytes. Clever-1 was found at all tested time points of pregnancy (weeks 12-38). Interestingly, one individual suffering from a mild pre-eclampsia had no detectable Clever-1 on the surface of the monocytes (FIG. 7).

Figure 8:
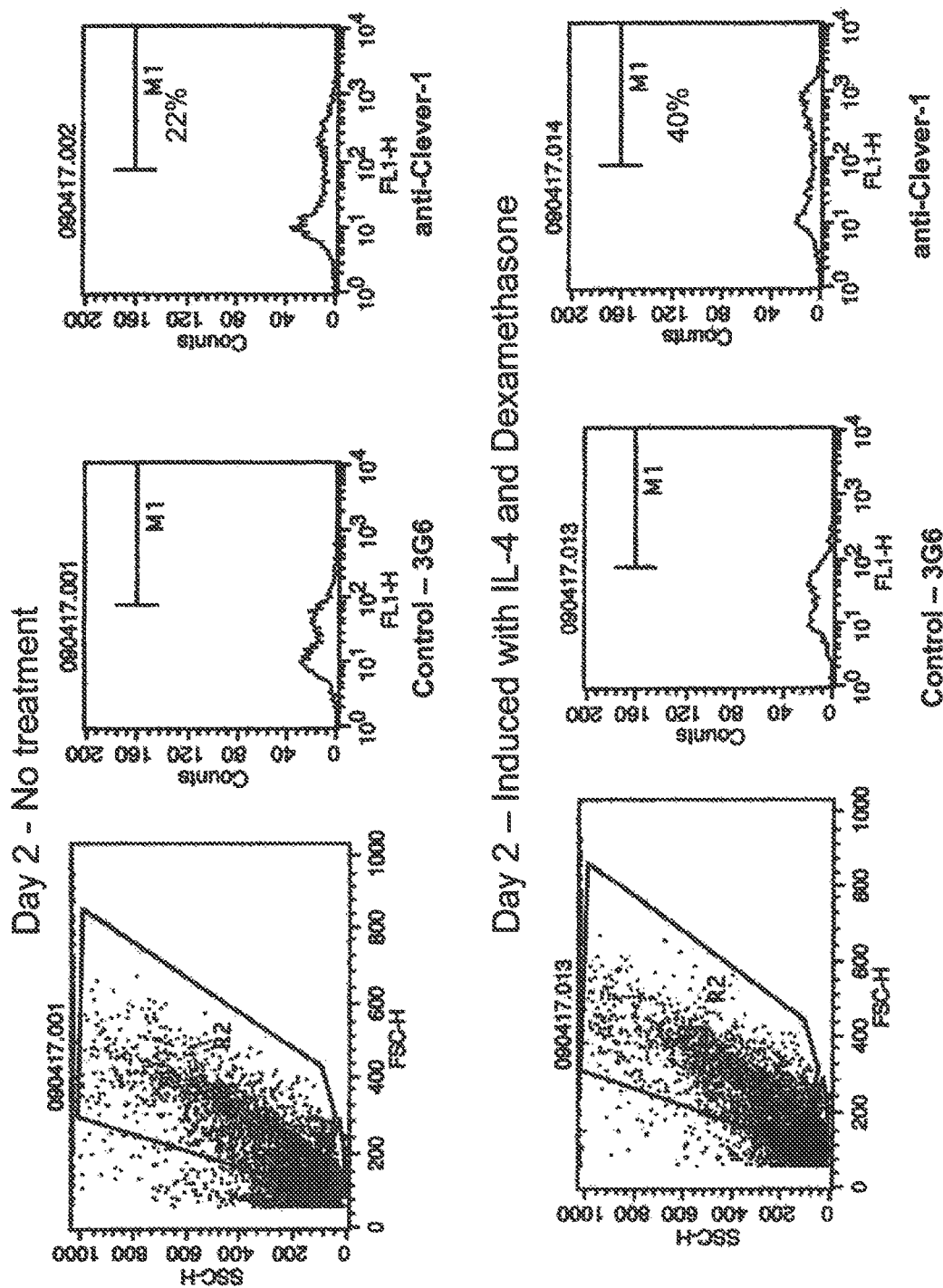
FIG. 8. Interleukin-4 and dexamethasone induce Clever-1 expression in placental macrophages. The forward and side scatters of the cells (R2) analyzed are shown without and with IL-4 and dexmethasone induction (2-days incubation). In the histograms the fluorescence intensity is in a logarithmic scale on the x axis and relative number of cells on y axis. The percentages shown on the right panels are obtained by deducting the percentage of the positive cells stained with the negative control antibody (=background).
Figure 9:
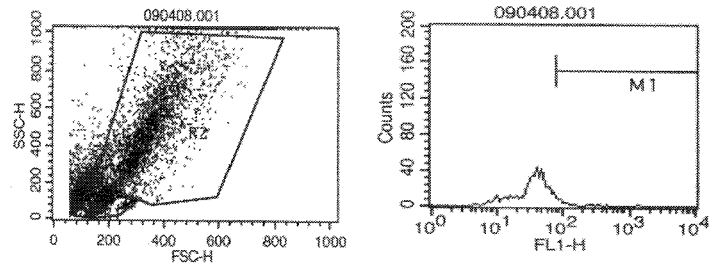
FIG. 9. Clever-1 expression can be downregulated by siRNA treatment. The treatments with a single siRNA species and pooled siRNAs targeting Clever-1 were used. Untreated and treatment with control siRNA are shown as comparison. The forward and side scatters of the cells (R2) analyzed are shown after indicated treatments. In the histograms the fluorescence intensity is in a logarithmic scale on the x axis and relative number of cells on y axis. The percentages shown on the right panels are obtained by deducting the percentage of the positive cells stained with the negative control antibody (=background).
Figure 9:
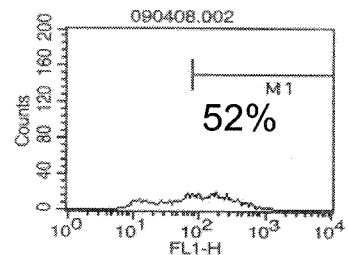
Figure 9:
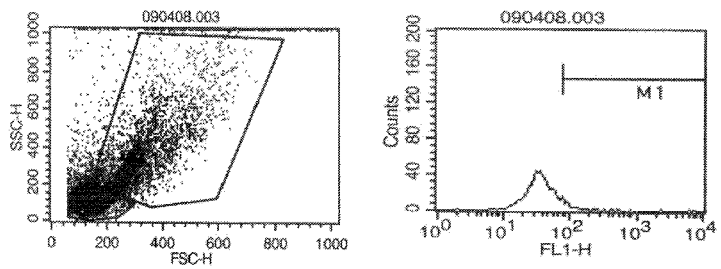
Figure 9:
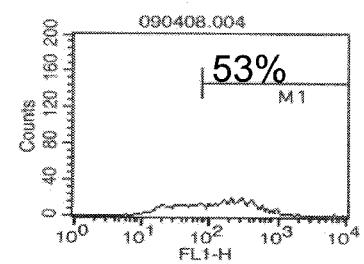
Figure 9:
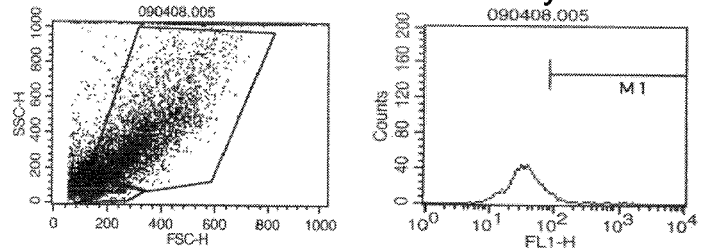
Figure 9:
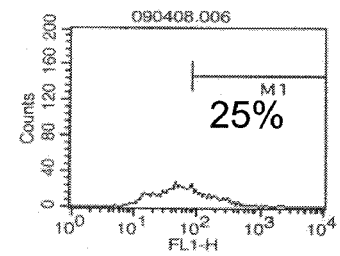
Figure 9:
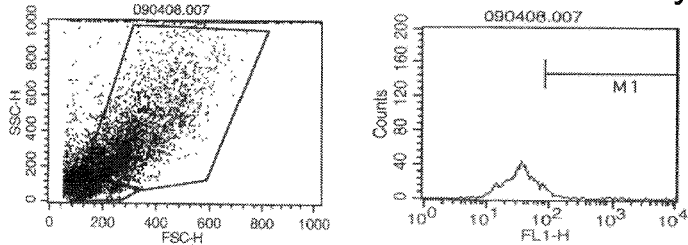
Figure 9:
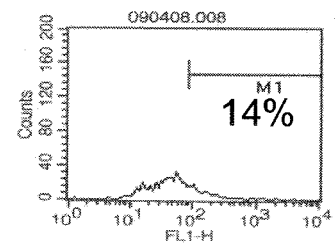

Expression of Clever-1 can be upregulated by interleukin-4 and dexamethasone and inhibited by siRNA. Two days incubation of placental monocytes with interleukin-4 and dexamethasone increases percentage of Clever-1 positive macrophages (FIG. 8). In contrast, the expression can be inhibited with Clever-1 specific siRNA but not with control siRNAs (FIG. 9).

Anti-Clever-1 antibodies interfere with normal pregnancy in mice. Mice were treated with a function blocking anti-mouse Clever-1 antibody or with an isotype-matched control antibody starting from day 1 of pregnancy. The treatments were given intravenously (100 µg mAb/injection) every third day until the delivery. When the mice gave birth, the litter-size was smaller in the mice treated with the anti-Clever-1 antibody when compared to the controls (in control 19 pups and in anti-Clever-1 treated mice 10 pups, n=3 mothers in both groups).

Discussion

Antitumor Effect:

Our work shows that anti-Clever-1 antibody therapy targets a unique subset of suppressive macrophages present in the tumors and leads to reduction in the number of regulatory T cells. Importantly, the antibody treatment does not markedly dampen immune response to the various antigens tested. Although the work has been performed using melanoma as a tumor model, our preliminary experiments with EL-4 lymphoma model indicate that the findings reported in this work are not restricted to melanoma.

Only few molecules present on afferent lymphatics such as macrophage mannose receptor, sphingosine- 1-phosphate receptor and CCL21 have been shown to mediate lymphocyte traffic via afferent lymphatic vessels (Marttila-Ichihara, F. et al. *Blood* 112:64-72). Among those Clever-1 is the first one, which is now shown to be involved in and druggable also at the suppressive arm of the anti-cancer immune response.

Tumor associated macrophages differentiate to type 2 macrophages within the tumor environment from the incoming blood monocytes (24). Direct cell-to-cell contact may be required for the differentiation, because peritoneal macrophages (outside the tumor) did not become MR positive in the presence of melanoma within the peritoneal cavity in our experiments (data not shown). About 65% of the MR positive type 2 tumor macrophages express Clever-1. Interestingly, anti-Clever-1 antibody treatment diminished both the number of MR+/Clever-1+ and MR+/Clever-1− macrophages. Presence of MR+/Clever-1+ macrophages within the tumor after the antibody therapy suggests that the antibody does not lead to complement mediated killing of these cells. Reduction of the number of MR+/Clever-1− macrophages, on the other hand, may indicate that also these cells express low levels of Clever-1 and targeting of Clever-1 prevents differentiation of these cells. Alternatively, inhibition of Clever-1 could potentially lead to changes in SPARC content within the tumor limiting the number of suppressive macrophages despite their Clever-1 expression status. SPARC that is endocytosed by Clever-1 has also been demonstrated to be an important component controlling tumor growth and dissemination in several types of cancer (Said, N. et al. *Mol. Cancer Res.* 5:1015-1030; Chlenski, A. et al. Cancer Res. 62:7357-7363; Chlenski, A.

et al. *Int. J. Cancer* 118:310-316 and Brekken, R. A. et al. *J. Clin. Invest.* 111:487-495) and could also be regulating the tumor growth in our setting.

The role vascular Clever-1 in the entrance of blood borne monocytes into the melanoma may be ruled out, because the blood vasculature of the B16 melanoma does not express Clever-1. Theoretically it is also possible that Clever-1 on monocytes/macrophages is involved in their entrance from the blood into the primary tumors and antibody therapy inhibits that function.

Type 2 macrophages secrete IL-10 that is immunosuppressive and various chemokines, especially CCL17 and CCL22 which attract CCR4 positive regulatory T cells (Sica, A. et al., *Cancer Lett.* 267:204-215). The reduction of regulatory T cells observed in our work can therefore, may be considered as a consequence of the reduction of type 2 macrophages, especially those expressing Clever-1 i.e type 3 macrophages. Their diminished number and functional capacity may also lower antigen specific tumor cell suppression and the over all immune balance switches from pro-tumoral to anti-tumoral.

Importantly, despite the antibody therapy was effective in the tumor treatment, it did not markedly diminish the immune response against various types of antigens. Reasons behind this may be that the antigens get into the lymph nodes in sufficient quantities to create immune response. Moreover, although the therapy presumably reduces lymphocyte trafficking into and out from the lymph node undergoing the immune response, it does not significantly alter the balance between the entrance of lymphocytes via HEV and their exit from the lymph nodes. Antibodies once created seem to circulate independently of Clever-1 in the body. Remarkably, the macrophages within the lymph nodes during the immune response remained Clever-1 negative although many of them brightly expressed MR. This indicates that MR positive macrophages within the tumors and lymph nodes undergoing the immune response belong to different subtypes. This may also explain, why the antibody therapy targeting Clever-1 during immunization does not have any effect on the number of MR positive macrophages and regulatory T cells.

In summary, our results indicate that Clever-1 is involved in different control points determining cancer growth and dissemination. As the successful treatment of cancer patients frequently requires different combinations of drugs, anti-Clever-1 antibody or another Clever-1 antagonist may be a beneficial addition into the armamentarium used to fight against cancer.

Fetomaternal Tolerance:

We report here that a very prominent population of Clever-1 positive macrophages is present in human placenta. Moreover, Clever-1 is found on the surface of circulating blood monocytes in normal pregnant women, but not (or in very low numbers) in age- and sex-matched control persons. However, in a pre-eclamptic patient, induction of Clever-1 was not seen on the blood monocytes. Finally, an anti-Clever-1 antibody treatment during the course of pregnancy diminished litter-sizes in mice. Together these data suggest that Clever-1 positive cell population is immune suppressive, and that it contributes to the induction of normal tolerance during the pregnancy.

Clever-1 is expressed on a subpopulation of type 2 macrophages in humans and mice. Type 2 macrophages have been shown to be immune suppressing in multiple experimental settings in mice. However, since Clever-1 is not expressed in all type 2 macrophages (normally defined as macrophage mannose receptor positive cells), we propose that a subpopulation of these cells (type 3 macrophages) can be further identified based on Clever-1 expression.

We have shown that type 3 macrophages are normally induced in the placenta and blood circulation during pregnancy. It is known that the induction of Clever-1 can be seen in normal blood monocytes (non-pregnant persons) through stimulation with immune suppressing molecules such as interleukin-4, interleukin-13 or dexamethasone. Probably these, or other anti-inflammatory molecules and steroid hormones, are responsible for Clever-1 induction during pregnancy. We propose that type 3 macrophages are immune suppressing in nature and serve to maintain feto-maternal tolerance in vivo.

Failure to induce Clever-1 in pregnancy may lead to loss of tolerance and manifestations of feto-maternal incompatibility. In early pregnancy this may manifest as spontaneous abortions, and later as conditions like pre-eclampsia. Therefore, induction of Clever-1 on blood monocytes may reflect the level of immune tolerance in the mother, and be useful for early detection of pre-eclampsia. Moreover, therapeutic induction of Clever-1 expressing type 3 macrophages by agents such as interleukins or steroids may be beneficial in boosting tolerance during the pregnancy.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A method of reducing the size and/or growth of a tumor, comprising:
    a) obtaining a tumor or body fluid from a cancer patient and a control sample;
    b) contacting the tumor or body fluid and the control sample with monoclonal antibody 3-266 (DSM ACC2519) or monoclonal antibody 3-372 (DSM ACC2590) and a monoclonal antibody against macrophage mannose receptor;
    c) detecting type 3 macrophages which express both a mannose receptor and Clever-1 protein in the tumor or body fluid by quantifying the amount of binding between the antibodies and the macrophage mannose receptor or the Clever-1 protein in the tumor or body fluid and in the control sample, wherein an elevated level of macrophage mannose receptor and Clever-1 protein in the tumor or body fluid indicates the presence of type 3 macrophages and that the size and/or growth of the tumor will be reduced by anti-Clever-1 therapy in the cancer patient; and
    d) treating the cancer patient with anti-Clever-1 antibodies capable of counteracting the influence of or down-regulating the expression of a Clever-1 protein;
    wherein the Clever-1 protein is encoded by the nucleic acid sequence of SEQ ID NO. 1, wherein said anti-Clever-1 antibodies are selected from the group consisting of monoclonal antibody 3-266 (DSM ACC2519), monoclonal antibody 3-372 (DSM ACC2590) and chimeric, humanized or primatized variants of monoclonal antibody 3-266 (DSM ACC2519) or monoclonal antibody 3-372 (DSM ACC2590), and wherein said chimeric, humanized or primatized variants have the same six CDRs as monoclonal antibody 3-266 (DSM ACC2519) or monoclonal antibody 3-372 (DSM ACC2590).

2. The method of claim 1, wherein the cancer patient is a melanoma patient.

3. The method according to claim 1, wherein said anti-Clever-1 antibody is monoclonal antibody 3-266 (DSM ACC2519) or monoclonal antibody 3-372 (DSM ACC2590).

4. A method of treating a patient having an elevated level of Clever-1 protein in a tumor or body fluid, comprising:
    a) obtaining a tumor or body fluid from the cancer patient and a control sample;
    b) contacting the tumor or body fluid and the control sample with monoclonal antibody 3-266 (DSM ACC2519) or monoclonal antibody 3-372 (DSM ACC2590) and a monoclonal antibody against macrophage mannose receptor;
    c) detecting an elevated level of macrophage mannose receptor and Clever-1 protein in the tumor or body fluid by quantifying the amount of binding between the antibodies and the macrophage mannose receptor and Clever-1 protein in the tumor sample and in the control sample; and
    d) administering an anti-Clever-1 antibody capable of counteracting the influence of or down-regulating the expression of the Clever-1 protein to the patient, if the patient displays an elevated level of macrophage mannose receptor and Clever-1 protein in the tumor or body fluid;

wherein the Clever-1 protein is encoded by the nucleic acid sequence of SEQ ID NO. 1, wherein said anti-Clever-1 antibody is selected from the group consisting of monoclonal antibody 3-266 (DSM ACC2519), monoclonal antibody 3-372 (DSM ACC2590) and chimeric, humanized or primatized variants of monoclonal antibody 3-266 (DSM ACC2519) or monoclonal antibody 3-372 (DSM ACC2590), and wherein said chimeric, humanized or primatized variants have the same six CDRs as monoclonal antibody 3-266 (DSM ACC2519) or monoclonal antibody 3-372 (DSM ACC2590).

5. The method of claim 4, wherein the cancer patient is a melanoma patient.

6. The method according to claim 4, wherein said anti-Clever-1 antibody is monoclonal antibody 3-266 (DSM ACC2519) or monoclonal antibody 3-372 (DSM ACC2590).

* * * * *

SEQUENCE LISTING

```
<160> NUMBER OF SEQ ID NOS: 1

<210> SEQ ID NO 1
<211> LENGTH: 7879
<212> TYPE: DNA
<213> ORGANISM: Homo sapiens
<220> FEATURE:
<221> NAME/KEY: exon
<222> LOCATION: (31)..(7740)

<400> SEQUENCE: 1
actctgtcct ggacagcgtg cccaccagcc atg gcg ggg ccc cgg ggc ctc ctc      54
                                 Met Ala Gly Pro Arg Gly Leu Leu
                                  1               5
```

-continued

| | |
|---|---|
| cca ctc tgc ctc ctg gcc ttc tgc ctg gca ggc ttc agc ttc gtc agg<br>Pro Leu Cys Leu Leu Ala Phe Cys Leu Ala Gly Phe Ser Phe Val Arg<br>10                      15                       20 | 102 |
| ggg cag gtg ctg ttc aaa ggc tgt gat gtg aaa acc acg ttt gtc act<br>Gly Gln Val Leu Phe Lys Gly Cys Asp Val Lys Thr Thr Phe Val Thr<br>25                      30                    35                 40 | 150 |
| cat gta ccc tgc acc tcg tgc gcg gcc atc aag aag cag acg tgt ccc<br>His Val Pro Cys Thr Ser Cys Ala Ala Ile Lys Lys Gln Thr Cys Pro<br>                  45                    50                       55 | 198 |
| tca ggc tgg ctg cgg gag ctc ccg gat cag ata acc cag gac tgc cgc<br>Ser Gly Trp Leu Arg Glu Leu Pro Asp Gln Ile Thr Gln Asp Cys Arg<br>                      60                    65                    70 | 246 |
| tac gaa gta cag ctg ggg ggc tct atg gtg tcc atg agc ggc tgc aga<br>Tyr Glu Val Gln Leu Gly Gly Ser Met Val Ser Met Ser Gly Cys Arg<br>              75                    80                    85 | 294 |
| cgg aag tgc cgg aag caa gtg gtg cag aag gcc tgc tgc cct ggc tac<br>Arg Lys Cys Arg Lys Gln Val Val Gln Lys Ala Cys Cys Pro Gly Tyr<br>       90                    95                    100 | 342 |
| tgg ggt tcc cgg tgc cat gaa tgc cct ggg ggc gct gag acc cca tgc<br>Trp Gly Ser Arg Cys His Glu Cys Pro Gly Gly Ala Glu Thr Pro Cys<br>105                    110                  115                  120 | 390 |
| aat ggc cac ggg acc tgc ttg gat ggc atg gac agg aat ggg acc tgt<br>Asn Gly His Gly Thr Cys Leu Asp Gly Met Asp Arg Asn Gly Thr Cys<br>                    125                  130                  135 | 438 |
| gtg tgc cag gaa aac ttc cgc ggc tca gcc tgc cag gag tgc caa gac<br>Val Cys Gln Glu Asn Phe Arg Gly Ser Ala Cys Gln Glu Cys Gln Asp<br>          140                  145                  150 | 486 |
| ccc aac cgg ttc ggg cct gac tgc caa tcg gtg tgc agc tgt gtg cac<br>Pro Asn Arg Phe Gly Pro Asp Cys Gln Ser Val Cys Ser Cys Val His<br>          155                  160                  165 | 534 |
| gga gtg tgc aac cat ggg cca cgt ggg gat gga agc tgc ctg tgc ttt<br>Gly Val Cys Asn His Gly Pro Arg Gly Asp Gly Ser Cys Leu Cys Phe<br>170                    175                  180 | 582 |
| gct gga tac act ggc ccc cac tgt gat caa gag ctg ccc gtc tgc cag<br>Ala Gly Tyr Thr Gly Pro His Cys Asp Gln Glu Leu Pro Val Cys Gln<br>185                    190                  195                  200 | 630 |
| gag ctg cgc tgt ccc cag aac acc cag tgc tcc gca gag gct ccc agc<br>Glu Leu Arg Cys Pro Gln Asn Thr Gln Cys Ser Ala Glu Ala Pro Ser<br>                    205                  210                  215 | 678 |
| tgc agg tgc ctg ccc ggc tac aca cag cag ggc agt gaa tgc gag gcc<br>Cys Arg Cys Leu Pro Gly Tyr Thr Gln Gln Gly Ser Glu Cys Arg Ala<br>          220                  225                  230 | 726 |
| ccc aac ccc tgc tgg cca tca ccc tgc tca ctg ctg gcc cag tgc tcg<br>Pro Asn Pro Cys Trp Pro Ser Pro Cys Ser Leu Leu Ala Gln Cys Ser<br>235                    240                  245 | 774 |
| gtg agc ccc aag ggg cag gct cag tgt cac tgc cct gag aac tac cat<br>Val Ser Pro Lys Gly Gln Ala Gln Cys His Cys Pro Glu Asn Tyr His<br>250                    255                  260 | 822 |
| ggc gat ggg atg gtg tgt ctg ccc aag gac cca tgc act gac aac ctt<br>Gly Asp Gly Met Val Cys Leu Pro Lys Asp Pro Cys Thr Asp Asn Leu<br>265                    270                  275                  280 | 870 |
| ggt ggc tgc ccc agc aac tct act ttg tgt gta tac cag aag ccg ggc<br>Gly Gly Cys Pro Ser Asn Ser Thr Leu Cys Val Tyr Gln Lys Pro Gly<br>                    285                  290                  295 | 918 |
| cag gcc ttc tgc acc tgc cgg cca ggc ctg gtc agc atc aac agc aac<br>Gln Ala Phe Cys Thr Cys Arg Pro Gly Leu Val Ser Ile Asn Ser Asn<br>                    300                  305                  310 | 966 |
| gct tct gcg ggc tgc ttc gcc ttc tgc tcc ccc ttc tcc tgc gac cgg<br>Ala Ser Ala Gly Cys Phe Ala Phe Cys Ser Pro Phe Ser Cys Asp Arg<br>                    315                  320                  325 | 1014 |

```
tct gcc act tgc cag gtg acc gct gat ggg aag acc agc tgt gtg tgc    1062
Ser Ala Thr Cys Gln Val Thr Ala Asp Gly Lys Thr Ser Cys Val Cys
    330                 335                 340 agg gaa agc gag gtg ggg gat ggg cgt gcc tgc tac gga cac ctg ctc    1110
Arg Glu Ser Glu Val Gly Asp Gly Arg Ala Cys Tyr Gly His Leu Leu
345                 350                 355                 360 cac gag gtg cag aag gcc acg cag aca ggc cgg gtg ttc ctg cag ctg    1158
His Glu Val Gln Lys Ala Thr Gln Thr Gly Arg Val Phe Leu Gln Leu
                365                 370                 375 agg gtc gcc gtg gcc atg atg gac cag ggc tgc cgg gaa atc ctt acc    1206
Arg Val Ala Val Ala Met Met Asp Gln Gly Cys Arg Glu Ile Leu Thr
            380                 385                 390 aca gcg ggc cct ttc acc gtg ctg gtg cca tcc gtc tcc tcc ttc tcc    1254
Thr Ala Gly Pro Phe Thr Val Leu Val Pro Ser Val Ser Ser Phe Ser
        395                 400                 405 tcc agg acc atg aat gca tcc ctt gcc cag cag ctc tgt aga cag cac    1302
Ser Arg Thr Met Asn Ala Ser Leu Ala Gln Gln Leu Cys Arg Gln His
    410                 415                 420 atc atc gca ggg cag cac atc ctg gag gac aca agg acc caa caa aca    1350
Ile Ile Ala Gly Gln His Ile Leu Glu Asp Thr Arg Thr Gln Gln Thr
425                 430                 435                 440 cga agg tgg tgg acg ctg gcc ggg cag gag atc acc gtc acc ttt aac    1398
Arg Arg Trp Trp Thr Leu Ala Gly Gln Glu Ile Thr Val Thr Phe Asn
                445                 450                 455 caa ttc acg aaa tac tcc tac aag tac aaa gac cag ccc cag cag acg    1446
Gln Phe Thr Lys Tyr Ser Tyr Lys Tyr Lys Asp Gln Pro Gln Gln Thr
            460                 465                 470 ttc aac atc tac aag gcc aac aac ata gca gct aat ggc gtc ttc cac    1494
Phe Asn Ile Tyr Lys Ala Asn Asn Ile Ala Ala Asn Gly Val Phe His
        475                 480                 485 gtg gtc act ggc ctg cgg tgg cag gcc ccc tct ggg acc cct ggg gat    1542
Val Val Thr Gly Leu Arg Trp Gln Ala Pro Ser Gly Thr Pro Gly Asp
    490                 495                 500 ccc aag aga act atc gga cag atc ctc gcc tct acc gag gcc ttc agc    1590
Pro Lys Arg Thr Ile Gly Gln Ile Leu Ala Ser Thr Glu Ala Phe Ser
505                 510                 515                 520 cgc ttt gaa acc atc ctg gag aac tgt ggg ctg ccc tcc atc ctg gac    1638
Arg Phe Glu Thr Ile Leu Glu Asn Cys Gly Leu Pro Ser Ile Leu Asp
                525                 530                 535 gga cct ggg ccc ttc aca gtc ttt gcc cca agc aat gag gct gtg gac    1686
Gly Pro Gly Pro Phe Thr Val Phe Ala Pro Ser Asn Glu Ala Val Asp
            540                 545                 550 agc ttg cgt gac ggc cgc ctg atc tac ctc ttc aca gcg ggt ctc tct    1734
Ser Leu Arg Asp Gly Arg Leu Ile Tyr Leu Phe Thr Ala Gly Leu Ser
        555                 560                 565 aaa ctg cag gag ttg gtg cgg tac cac atc tac aac cac ggc cag ctg    1782
Lys Leu Gln Glu Leu Val Arg Tyr His Ile Tyr Asn His Gly Gln Leu
    570                 575                 580 acc gtt gag aag ctc atc tcc aag ggt cgg atc ctc acc atg gcg aac    1830
Thr Val Glu Lys Leu Ile Ser Lys Gly Arg Ile Leu Thr Met Ala Asn
585                 590                 595                 600 cag gtc ctg gct gtg aac att tct gag gag ggg cgc atc ctg ctg gga    1878
Gln Val Leu Ala Val Asn Ile Ser Glu Glu Gly Arg Ile Leu Leu Gly
                605                 610                 615 ccc gag ggg gtc ccg ctg cag agg gta gac gtg atg gcc gcc aat ggt    1926
Pro Glu Gly Val Pro Leu Gln Arg Val Asp Val Met Ala Ala Asn Gly
            620                 625                 630 gtg atc cac atg ctg gac ggc atc ctg ctg ccc ccg acc atc ctg ccc    1974
Val Ile His Met Leu Asp Gly Ile Leu Leu Pro Pro Thr Ile Leu Pro
```

-continued

```
                635                 640                 645
atc ctg ccc aag cac tgc agc gag gag cag cac aag att gtg gcg ggc    2022
Ile Leu Pro Lys His Cys Ser Glu Glu Gln His Lys Ile Val Ala Gly
    650                 655                 660 tcc tgt gtg gac tgc caa gcc ctg aac acc agc acg tgt ccc ccc aac    2070
Ser Cys Val Asp Cys Gln Ala Leu Asn Thr Ser Thr Cys Pro Pro Asn
665                 670                 675                 680 agt gtg aag ctg gac atc ttc ccc aag gag tgt gtc tac atc cat gac    2118
Ser Val Lys Leu Asp Ile Phe Pro Lys Glu Cys Val Tyr Ile His Asp
                685                 690                 695 cca acg ggg ctc aat gtg cta aag aag ggc tgt gcc agc tac tgc aac    2166
Pro Thr Gly Leu Asn Val Leu Lys Lys Gly Cys Ala Ser Tyr Cys Asn
            700                 705                 710 caa acc atc atg gaa caa ggc tgc tgc aaa ggt ttt ttc ggg cct gac    2214
Gln Thr Ile Met Glu Gln Gly Cys Cys Lys Gly Phe Phe Gly Pro Asp
        715                 720                 725 tgc acg cag tgt cct ggg ggc ttc tcc aac ccc tgc tat ggc aaa ggc    2262
Cys Thr Gln Cys Pro Gly Gly Phe Ser Asn Pro Cys Tyr Gly Lys Gly
    730                 735                 740 aat tgc agt gat ggg atc cag ggc aat ggg gcc tgc ctc tgc ttc cca    2310
Asn Cys Ser Asp Gly Ile Gln Gly Asn Gly Ala Cys Leu Cys Phe Pro
745                 750                 755                 760 gac tac aag ggc atc gcc tgc cac atc tgc tcg aac cca aac aag cat    2358
Asp Tyr Lys Gly Ile Ala Cys His Ile Cys Ser Asn Pro Asn Lys His
                765                 770                 775 gga gag caa tgc cag gaa gac tgc ggc tgt gtc cat ggt ctc tgc gac    2406
Gly Glu Gln Cys Gln Glu Asp Cys Gly Cys Val His Gly Leu Cys Asp
            780                 785                 790 aac cgc cca ggc agt ggg ggg gtg tgc cag cag ggc acg tgt gcc cct    2454
Asn Arg Pro Gly Ser Gly Gly Val Cys Gln Gln Gly Thr Cys Ala Pro
        795                 800                 805 ggc ttc agt ggc cgg ttc tgc aac gag tcc atg ggg gac tgt ggg ccc    2502
Gly Phe Ser Gly Arg Phe Cys Asn Glu Ser Met Gly Asp Cys Gly Pro
    810                 815                 820 aca ggg ctg gcc cag cac tgc cac ctg cat gcc cgc tgt gtt agc cag    2550
Thr Gly Leu Ala Gln His Cys His Leu His Ala Arg Cys Val Ser Gln
825                 830                 835                 840 gag ggt gtt gcc aga tgt cgc tgt ctt gat ggc ttt gag ggt gat ggc    2598
Glu Gly Val Ala Arg Cys Arg Cys Leu Asp Gly Phe Glu Gly Asp Gly
                845                 850                 855 ttc tcc tgc aca cct agc aac ccc tgc tcc cac ccg gac cgt gga ggc    2646
Phe Ser Cys Thr Pro Ser Asn Pro Cys Ser His Pro Asp Arg Gly Gly
            860                 865                 870 tgc tca gag aat gct gag tgt gtc cct ggg tcc ctg ggc acc cac cac    2694
Cys Ser Glu Asn Ala Glu Cys Val Pro Gly Ser Leu Gly Thr His His
        875                 880                 885 tgc aca tgc cac aaa ggc tgg agt ggg gat ggc cgc gtc tgt gtg gct    2742
Cys Thr Cys His Lys Gly Trp Ser Gly Asp Gly Arg Val Cys Val Ala
    890                 895                 900 att gac gag tgt gag ctg gac gtg aga ggt ggc tgc cac acc gat gcc    2790
Ile Asp Glu Cys Glu Leu Asp Val Arg Gly Gly Cys His Thr Asp Ala
905                 910                 915                 920 ctc tgc agc tat gtg ggc ccc ggg cag agc cga tgc acc tgc aag ctg    2838
Leu Cys Ser Tyr Val Gly Pro Gly Gln Ser Arg Cys Thr Cys Lys Leu
                925                 930                 935 ggc ttt gcc ggg gat ggc tac cag tgc agc ccc atc gac ccc tgc cgg    2886
Gly Phe Ala Gly Asp Gly Tyr Gln Cys Ser Pro Ile Asp Pro Cys Arg
            940                 945                 950 gca ggc aat ggc ggc tgc cac ggc ctg gcc acc tgc cgg gca gtg ggg    2934
```

```
            Ala Gly Asn Gly Gly Cys His Gly Leu Ala Thr Cys Arg Ala Val Gly
                        955                 960                 965 gga ggt cag cgg gtc tgc acg tgc ccc cct ggc ttt ggg ggt gat ggc           2982
Gly Gly Gln Arg Val Cys Thr Cys Pro Pro Gly Phe Gly Gly Asp Gly
            970                 975                 980 ttc agc tgt tat gga gac atc ttc cgg gag ctg gag gca aat gcc cac           3030
Phe Ser Cys Tyr Gly Asp Ile Phe Arg Glu Leu Glu Ala Asn Ala His
985                 990                 995                 1000 ttc tcc atc ttc tac caa tgg ctt aag agt gcc ggc atc acg ctt               3075
Phe Ser Ile Phe Tyr Gln Trp Leu Lys Ser Ala Gly Ile Thr Leu
                1005                1010                1015 cct gcc gac cgc cga gtc aca gcc ctg gtg ccc tcc gag gct gca               3120
Pro Ala Asp Arg Arg Val Thr Ala Leu Val Pro Ser Glu Ala Ala
            1020                1025                1030 gtc cgt cag ctg agc ccc gag gac cga gct ttc tgg ctg cag cca               3165
Val Arg Gln Leu Ser Pro Glu Asp Arg Ala Phe Trp Leu Gln Pro
            1035                1040                1045 agg acg ctg ccg aac ctg gtc agg gcc cat ttt ctc cag ggt gcc               3210
Arg Thr Leu Pro Asn Leu Val Arg Ala His Phe Leu Gln Gly Ala
            1050                1055                1060 ctc ttc gag gag gag ctg gcc cgg ctg ggt ggg cag gaa gtg gcc               3255
Leu Phe Glu Glu Glu Leu Ala Arg Leu Gly Gly Gln Glu Val Ala
            1065                1070                1075 acc ctg aac ccc acc aca cgc tgg gag att cgc aac att agt ggg               3300
Thr Leu Asn Pro Thr Thr Arg Trp Glu Ile Arg Asn Ile Ser Gly
            1080                1085                1090 agg gtc tgg gtg cag aat gcc agc gtg gat gtg gct gac ctc ctt               3345
Arg Val Trp Val Gln Asn Ala Ser Val Asp Val Ala Asp Leu Leu
            1095                1100                1105 gcc acc aac ggt gtc cta cac atc ctc agc cag gtc tta ctg ccc               3390
Ala Thr Asn Gly Val Leu His Ile Leu Ser Gln Val Leu Leu Pro
            1110                1115                1120 ccc cga ggg gat gtg ccc ggt ggg cag ggg ttg ctg cag cag ctg               3435
Pro Arg Gly Asp Val Pro Gly Gly Gln Gly Leu Leu Gln Gln Leu
            1125                1130                1135 gac ttg gtg cct gcc ttc agc ctc ttc cgg gaa ttg ctg cag cac               3480
Asp Leu Val Pro Ala Phe Ser Leu Phe Arg Glu Leu Leu Gln His
            1140                1145                1150 cat ggg ttg gtg ccc cag att gag gct gcc act gcc tac acc atc               3525
His Gly Leu Val Pro Gln Ile Glu Ala Ala Thr Ala Tyr Thr Ile
            1155                1160                1165 ttt gtg ccc acc aac cgc tcc ctg gag gcc cag ggc aac agc agt               3570
Phe Val Pro Thr Asn Arg Ser Leu Glu Ala Gln Gly Asn Ser Ser
            1170                1175                1180 cac ctg gac gca gac aca gtg cgg cac cat gtg gtc ctg ggg gag               3615
His Leu Asp Ala Asp Thr Val Arg His His Val Val Leu Gly Glu
            1185                1190                1195 gcc ctc tcc atg gaa acc ctg cgg aag ggt gga cac cgc aac tcc               3660
Ala Leu Ser Met Glu Thr Leu Arg Lys Gly Gly His Arg Asn Ser
            1200                1205                1210 ctc ctg ggc cct gcc cac tgg atc gtc ttc tac aac cac agt ggc               3705
Leu Leu Gly Pro Ala His Trp Ile Val Phe Tyr Asn His Ser Gly
            1215                1220                1225 cag cct gag gtg aac cat gtg cca ctg gaa ggc ccc atg ctg gag               3750
Gln Pro Glu Val Asn His Val Pro Leu Glu Gly Pro Met Leu Glu
            1230                1235                1240 gcc cct ggc cgc tcg ctg att ggt ctg tcg ggg gtc ctg acg gtg               3795
Ala Pro Gly Arg Ser Leu Ile Gly Leu Ser Gly Val Leu Thr Val
            1245                1250                1255
```

-continued

| | | |
|---|---|---|
| ggc tca agt cgc tgc ctg cat agc cac gct gag gcc ctg cgg gag<br>Gly Ser Ser Arg Cys Leu His Ser His Ala Glu Ala Leu Arg Glu<br>            1260                  1265                  1270 | 3840 |
| aaa tgt gta aac tgc acc agg aga ttc cgc tgc act cag ggc ttc<br>Lys Cys Val Asn Cys Thr Arg Arg Phe Arg Cys Thr Gln Gly Phe<br>            1275                  1280                  1285 | 3885 |
| cag ctg cag gac aca ccc agg aag agc tgt gtc tac cga tct ggc<br>Gln Leu Gln Asp Thr Pro Arg Lys Ser Cys Val Tyr Arg Ser Gly<br>            1290                  1295                  1300 | 3930 |
| ttc tcc ttc tcc cgg ggc tgc tct tac aca tgt gcc aag aag atc<br>Phe Ser Phe Ser Arg Gly Cys Ser Tyr Thr Cys Ala Lys Lys Ile<br>            1305                  1310                  1315 | 3975 |
| cag gtg ccg gac tgc tgc cct ggt ttc ttt ggc acg ctg tgt gag<br>Gln Val Pro Asp Cys Cys Pro Gly Phe Phe Gly Thr Leu Cys Glu<br>            1320                  1325                  1330 | 4020 |
| cca tgc cca ggg ggt cta ggg ggg gtg tgc tca ggc cat ggg cag<br>Pro Cys Pro Gly Gly Leu Gly Gly Val Cys Ser Gly His Gly Gln<br>            1335                  1340                  1345 | 4065 |
| tgc cag gac agg ttc ctg ggc agc ggg gag tgc cac tgc cac gag<br>Cys Gln Asp Arg Phe Leu Gly Ser Gly Glu Cys His Cys His Glu<br>            1350                  1355                  1360 | 4110 |
| ggc ttc cat gga acg gcc tgt gag gtg tgt gag ctg ggc cgc tac<br>Gly Phe His Gly Thr Ala Cys Glu Val Cys Glu Leu Gly Arg Tyr<br>            1365                  1370                  1375 | 4155 |
| ggg ccc aac tgc acc gga gtg tgt gac tgt gcc cat ggg ctg tgc<br>Gly Pro Asn Cys Thr Gly Val Cys Asp Cys Ala His Gly Leu Cys<br>            1380                  1385                  1390 | 4200 |
| cag gag ggg ctg caa ggg gac gga agc tgt gtc tgt aac gtg ggc<br>Gln Glu Gly Leu Gln Gly Asp Gly Ser Cys Val Cys Asn Val Gly<br>            1395                  1400                  1405 | 4245 |
| tgg cag ggc ctc cgc tgt gac cag aaa atc acc agc cct cag tgc<br>Trp Gln Gly Leu Arg Cys Asp Gln Lys Ile Thr Ser Pro Gln Cys<br>            1410                  1415                  1420 | 4290 |
| cct agg aag tgc gac ccc aat gcc aac tgc gtg cag gac tcg gcc<br>Pro Arg Lys Cys Asp Pro Asn Ala Asn Cys Val Gln Asp Ser Ala<br>            1425                  1430                  1435 | 4335 |
| gga gcc tcc acc tgc gcc tgt gct gcg gga tac tcc ggc aat ggc<br>Gly Ala Ser Thr Cys Ala Cys Ala Ala Gly Tyr Ser Gly Asn Gly<br>            1440                  1445                  1450 | 4380 |
| atc ttc tgt tca gag gtg gac ccc tgc gcc cac ggc cat ggg ggc<br>Ile Phe Cys Ser Glu Val Asp Pro Cys Ala His Gly His Gly Gly<br>            1455                  1460                  1465 | 4425 |
| tgc tcc cct cat gcc aac tgt acc aag gtg gca cct ggg cag cgg<br>Cys Ser Pro His Ala Asn Cys Thr Lys Val Ala Pro Gly Gln Arg<br>            1470                  1475                  1480 | 4470 |
| aca tgc acc tgc cag gat ggc tac atg ggc gac ggg gag ctg tgc<br>Thr Cys Thr Cys Gln Asp Gly Tyr Met Gly Asp Gly Glu Leu Cys<br>            1485                  1490                  1495 | 4515 |
| cag gaa att aac agc tgt ctc atc cac cac ggg ggc tgc cac att<br>Gln Glu Ile Asn Ser Cys Leu Ile His His Gly Gly Cys His Ile<br>            1500                  1505                  1510 | 4560 |
| cac gcc gag tgc atc ccc act ggc ccc cag cag gtc tcc tgc agc<br>His Ala Glu Cys Ile Pro Thr Gly Pro Gln Gln Val Ser Cys Ser<br>            1515                  1520                  1525 | 4605 |
| tgc cgt gag ggt tac agc ggg gat ggc atc cgg acc tgc gag ctc<br>Cys Arg Glu Gly Tyr Ser Gly Asp Gly Ile Arg Thr Cys Glu Leu<br>            1530                  1535                  1540 | 4650 |
| ctg gac ccc tgc tct aag aac aat gga gga tgc agc cca tat gcc<br>Leu Asp Pro Cys Ser Lys Asn Asn Gly Gly Cys Ser Pro Tyr Ala<br>            1545                  1550                  1555 | 4695 |

```
acc tgc aaa agc aca  ggg gat ggc cag agg  aca tgt acc tgc gac           4740
Thr Cys Lys Ser Thr  Gly Asp Gly Gln Arg  Thr Cys Thr Cys Asp
            1560                1565                     1570 aca gcc cac acc gtg  ggg gac ggc ctc acc  tgc gtg gcc cga gtc           4785
Thr Ala His Thr Val  Gly Asp Gly Leu Thr  Cys Val Ala Arg Val
        1575                    1580                 1585 ggc ctg gag ctc ctg  agg gat aag cat gcc  tca ttc ttc agc ctc           4830
Gly Leu Glu Leu Leu  Arg Asp Lys His Ala  Ser Phe Phe Ser Leu
        1590                    1595                 1600 cgc ctc ctg gaa tat  aag gag ctc aag ggc  gat ggg cct ttc acc           4875
Arg Leu Leu Glu Tyr  Lys Glu Leu Lys Gly  Asp Gly Pro Phe Thr
        1605                    1610                 1615 atc ttc gtg ccg cac  gca gat cta atg agc  aac ctg tcg cag gat           4920
Ile Phe Val Pro His  Ala Asp Leu Met Ser  Asn Leu Ser Gln Asp
        1620                    1625                 1630 gag ctg gcc cgg att  cgt gcg cat cgc cag  ctg gtg ttt cgc tac           4965
Glu Leu Ala Arg Ile  Arg Ala His Arg Gln  Leu Val Phe Arg Tyr
        1635                    1640                 1645 cac gtg gtt ggc tgt  cgg cgg ctg cgg agc  gag gac ctg ctg gag           5010
His Val Val Gly Cys  Arg Arg Leu Arg Ser  Glu Asp Leu Leu Glu
        1650                    1655                 1660 cag ggg tac gcc acg  gcc ctc tca ggg cac  cca ctg cgc ttc agc           5055
Gln Gly Tyr Ala Thr  Ala Leu Ser Gly His  Pro Leu Arg Phe Ser
        1665                    1670                 1675 gag agg gag ggc agc  ata tac ctc aat gac  ttc gcg cgc gtg gtg           5100
Glu Arg Glu Gly Ser  Ile Tyr Leu Asn Asp  Phe Ala Arg Val Val
        1680                    1685                 1690 agc agc gac cat gag  gcc gtg aac ggc atc  ctg cac ttc att gac           5145
Ser Ser Asp His Glu  Ala Val Asn Gly Ile  Leu His Phe Ile Asp
        1695                    1700                 1705 cgt gtc ctg ctg ccc  ccc gag gcg ctg cac  tgg gag cct gat gat           5190
Arg Val Leu Leu Pro  Pro Glu Ala Leu His  Trp Glu Pro Asp Asp
        1710                    1715                 1720 gct ccc atc ccg agg  aga aat gtc acc gcc  gcc gcc cag ggc ttc           5235
Ala Pro Ile Pro Arg  Arg Asn Val Thr Ala  Ala Ala Gln Gly Phe
        1725                    1730                 1735 ggt tac aag atc ttc  agc ggc ctc ctg aag  gtg gcc ggc ctc ctg           5280
Gly Tyr Lys Ile Phe  Ser Gly Leu Leu Lys  Val Ala Gly Leu Leu
        1740                    1745                 1750 ccc ctg ctt cga gag  gca tcc cat agg ccc  ttc aca atg ctg tgg           5325
Pro Leu Leu Arg Glu  Ala Ser His Arg Pro  Phe Thr Met Leu Trp
        1755                    1760                 1765 ccc aca gac gcc gcc  ttt cga gct ctg cct  ccg gat cgc cag gcc           5370
Pro Thr Asp Ala Ala  Phe Arg Ala Leu Pro  Pro Asp Arg Gln Ala
        1770                    1775                 1780 tgg ctg tac cat gag  gac cac cgt gac aag  cta gca gcc att ctg           5415
Trp Leu Tyr His Glu  Asp His Arg Asp Lys  Leu Ala Ala Ile Leu
        1785                    1790                 1795 cgg ggc cac atg att  cgc aat gtc gag gcc  ttg gca tct gac ctg           5460
Arg Gly His Met Ile  Arg Asn Val Glu Ala  Leu Ala Ser Asp Leu
        1800                    1805                 1810 ccc aac ctg ggc cca  ctt cga acc atg cat  ggg acc ccc atc tct           5505
Pro Asn Leu Gly Pro  Leu Arg Thr Met His  Gly Thr Pro Ile Ser
        1815                    1820                 1825 ttc tcc tgc agc cga  acg cgg ccc ggt gag  ctc atg gtg ggt gag           5550
Phe Ser Cys Ser Arg  Thr Arg Pro Gly Glu  Leu Met Val Gly Glu
        1830                    1835                 1840 gat gat gct cgc att  gtg cag cgg cac ttg  ccc ttt gag ggt ggc           5595
Asp Asp Ala Arg Ile  Val Gln Arg His Leu  Pro Phe Glu Gly Gly
```

```
                    1845            1850            1855
ctg gcc tat ggc atc gac cag ctg ctg gag cca cct ggc ctt ggt       5640
Leu Ala Tyr Gly Ile Asp Gln Leu Leu Glu Pro Pro Gly Leu Gly
                    1860            1865            1870 gct cgc tgt gac cac ttt gag acc cgg ccc ctg cga ctg aac acc       5685
Ala Arg Cys Asp His Phe Glu Thr Arg Pro Leu Arg Leu Asn Thr
                    1875            1880            1885 tgc agc atc tgt ggg ctg gag cca ccc tgt cct gag ggg tca cag       5730
Cys Ser Ile Cys Gly Leu Glu Pro Pro Cys Pro Glu Gly Ser Gln
                    1890            1895            1900 gag cag ggc agc cct gag gcc tgc tgg cgc ttc tac ccg aag ttc       5775
Glu Gln Gly Ser Pro Glu Ala Cys Trp Arg Phe Tyr Pro Lys Phe
                    1905            1910            1915 tgg acg tcc cct ccg ctg cac tct ttg gga tta cgc agc gtc tgg       5820
Trp Thr Ser Pro Pro Leu His Ser Leu Gly Leu Arg Ser Val Trp
                    1920            1925            1930 gtc cac ccc agc ctt tgg ggt agg ccc caa ggc ctg ggc agg ggc       5865
Val His Pro Ser Leu Trp Gly Arg Pro Gln Gly Leu Gly Arg Gly
                    1935            1940            1945 tgc cac cgc aat tgt gtc acc acc acc tgg aag ccc agc tgc tgc       5910
Cys His Arg Asn Cys Val Thr Thr Thr Trp Lys Pro Ser Cys Cys
                    1950            1955            1960 cct ggt cac tat ggc agt gag tgc caa gct tgc cct ggc ggc ccc       5955
Pro Gly His Tyr Gly Ser Glu Cys Gln Ala Cys Pro Gly Gly Pro
                    1965            1970            1975 agc agc cct tgt agt gac cgt ggc gtg tgc atg gac ggc atg agt       6000
Ser Ser Pro Cys Ser Asp Arg Gly Val Cys Met Asp Gly Met Ser
                    1980            1985            1990 ggc agt ggg cag tgt ctg tgc cgt tca ggt ttt gct ggg aca gcc       6045
Gly Ser Gly Gln Cys Leu Cys Arg Ser Gly Phe Ala Gly Thr Ala
                    1995            2000            2005 tgt gaa ctc tgt gct cct ggt gcc ttt ggg ccc cat tgt caa gcc       6090
Cys Glu Leu Cys Ala Pro Gly Ala Phe Gly Pro His Cys Gln Ala
                    2010            2015            2020 tgc cgc tgc act gtg cat ggc cgc tgt gat gag ggc ctt ggg ggc       6135
Cys Arg Cys Thr Val His Gly Arg Cys Asp Glu Gly Leu Gly Gly
                    2025            2030            2035 tct ggc tcc tgc ttc tgt gat gaa ggc tgg act ggg cca cgc tgt       6180
Ser Gly Ser Cys Phe Cys Asp Glu Gly Trp Thr Gly Pro Arg Cys
                    2040            2045            2050 gag gtg caa ctg gag ctg cag cct gtg tgt acc cca ccc tgt gca       6225
Glu Val Gln Leu Glu Leu Gln Pro Val Cys Thr Pro Pro Cys Ala
                    2055            2060            2065 ccc gag gct gtg tgc cgt gca ggc aac agc tgt gag tgc agc ctg       6270
Pro Glu Ala Val Cys Arg Ala Gly Asn Ser Cys Glu Cys Ser Leu
                    2070            2075            2080 ggc tat gaa ggg gat ggc cgc gtg tgt aca gtg gca gac ctg tgc       6315
Gly Tyr Glu Gly Asp Gly Arg Val Cys Thr Val Ala Asp Leu Cys
                    2085            2090            2095 cag gac ggg cat ggt ggc tgc agt gag cac gcc aac tgt agc cag       6360
Gln Asp Gly His Gly Gly Cys Ser Glu His Ala Asn Cys Ser Gln
                    2100            2105            2110 gta gga aca atg gtc act tgt acc tgc ctg ccc gac tac gag ggt       6405
Val Gly Thr Met Val Thr Cys Thr Cys Leu Pro Asp Tyr Glu Gly
                    2115            2120            2125 gat ggc tgg agc tgc cgg gcc cgc aac ccc tgc aca gat ggc cac       6450
Asp Gly Trp Ser Cys Arg Ala Arg Asn Pro Cys Thr Asp Gly His
                    2130            2135            2140 cgc ggg ggc tgc agc gag cac gcc aac tgc ttg agc acc ggc ctg       6495
```

|  |  |  |  |  |  |  |  |  |  |  |  |  |
|---|---|---|---|---|---|---|---|---|---|---|---|---|
| Arg | Gly | Gly | Cys | Ser | Glu | His | Ala | Asn | Cys | Leu | Ser | Thr | Gly | Leu |
|  |  |  |  | 2145 |  |  |  | 2150 |  |  |  | 2155 |

```
aac aca cgg cgc tgt  gag tgc cac gca ggc  tac gta ggc gat gga        6540
Asn Thr Arg Arg Cys  Glu Cys His Ala Gly  Tyr Val Gly Asp Gly
            2160                 2165                 2170 ctg cag tgt ctg gag  gag tcg gaa cca cct  gtg gac cgc tgc ttg        6585
Leu Gln Cys Leu Glu  Glu Ser Glu Pro Pro  Val Asp Arg Cys Leu
            2175                 2180                 2185 ggc cag cca ccg ccc  tgc cac tca gat gcc  atg tgc act gac ctg        6630
Gly Gln Pro Pro Pro  Cys His Ser Asp Ala  Met Cys Thr Asp Leu
            2190                 2195                 2200 cac ttc cag gag aaa  cgg gct ggc gtt ttc  cac ctc cag gcc acc        6675
His Phe Gln Glu Lys  Arg Ala Gly Val Phe  His Leu Gln Ala Thr
            2205                 2210                 2215 agc ggc cct tat ggt  ctg aac ttt tcg gag  gct gag gcg gca tgc        6720
Ser Gly Pro Tyr Gly  Leu Asn Phe Ser Glu  Ala Glu Ala Ala Cys
            2220                 2225                 2230 gaa gca cag gga gcc  gtc ctt gct tca ttc  cct cag ctc tct gct        6765
Glu Ala Gln Gly Ala  Val Leu Ala Ser Phe  Pro Gln Leu Ser Ala
            2235                 2240                 2245 gcc cag cag ctg ggc  ttc cac ctg tgc ctc  atg ggc tgg ctg gcc        6810
Ala Gln Gln Leu Gly  Phe His Leu Cys Leu  Met Gly Trp Leu Ala
            2250                 2255                 2260 aat ggc tcc act gcc  cac cct gtg gtt ttc  cct gtg gcg gac tgt        6855
Asn Gly Ser Thr Ala  His Pro Val Val Phe  Pro Val Ala Asp Cys
            2265                 2270                 2275 ggc aat ggt cgg gtg  ggc gta gtc agc ctg  ggt gcc cgc aag aac        6900
Gly Asn Gly Arg Val  Gly Val Val Ser Leu  Gly Ala Arg Lys Asn
            2280                 2285                 2290 ctc tca gaa cgc tgg  gat gcc tac tgc ttc  cgt gtg caa gat gtg        6945
Leu Ser Glu Arg Trp  Asp Ala Tyr Cys Phe  Arg Val Gln Asp Val
            2295                 2300                 2305 gcc tgc cga tgc cga  aat ggc ttc gtg ggt  gac ggg atc agc acg        6990
Ala Cys Arg Cys Arg  Asn Gly Phe Val Gly  Asp Gly Ile Ser Thr
            2310                 2315                 2320 tgc aat ggg aag ctg  ctg gat gtg ctg gct  gcc act gcc aac ttc        7035
Cys Asn Gly Lys Leu  Leu Asp Val Leu Ala  Ala Thr Ala Asn Phe
            2325                 2330                 2335 tcc acc ttc tat ggg  atg cta ttg ggc tat  gcc aat gcc acc cag        7080
Ser Thr Phe Tyr Gly  Met Leu Leu Gly Tyr  Ala Asn Ala Thr Gln
            2340                 2345                 2350 cgg ggt ctc gac ttc  ctg gac ttc ctg gat  gat gag ctc acg tat        7125
Arg Gly Leu Asp Phe  Leu Asp Phe Leu Asp  Asp Glu Leu Thr Tyr
            2355                 2360                 2365 aag aca ctc ttc gtc  cct gtc aat gaa ggc  ttt gtg gac aac atg        7170
Lys Thr Leu Phe Val  Pro Val Asn Glu Gly  Phe Val Asp Asn Met
            2370                 2375                 2380 acg ctg agt ggc cca  gac ttg gag ctg cat  gcc tcc aac gcc acc        7215
Thr Leu Ser Gly Pro  Asp Leu Glu Leu His  Ala Ser Asn Ala Thr
            2385                 2390                 2395 ctc cta agt gcc aac  gcc agc cag ggg aag  ttg ctt ccg gcc cac        7260
Leu Leu Ser Ala Asn  Ala Ser Gln Gly Lys  Leu Leu Pro Ala His
            2400                 2405                 2410 tca ggc ctc agc ctc  atc atc agt gac gca  ggc cct gac aac agt        7305
Ser Gly Leu Ser Leu  Ile Ile Ser Asp Ala  Gly Pro Asp Asn Ser
            2415                 2420                 2425 tcc tgg gcc cct gtg  gcc cca ggg aca gtt  gtg gtt agc cgt atc        7350
Ser Trp Ala Pro Val  Ala Pro Gly Thr Val  Val Val Ser Arg Ile
            2430                 2435                 2440
```

-continued

| | | | | | | | | | | | | |
|---|---|---|---|---|---|---|---|---|---|---|---|---|
| att | gtg | tgg | gac | atc | atg | gcc | ttc | aat | ggc | atc | atc | cat | gct | ctg | 7395 |
| Ile | Val | Trp | Asp | Ile | Met | Ala | Phe | Asn | Gly | Ile | Ile | His | Ala | Leu |
| | | | | 2445 | | | | | 2450 | | | | | 2455 |
| gcc | agc | ccc | ctc | ctg | gca | ccc | cca | cag | ccc | cag | gca | gtg | ctg | gcg | 7440 |
| Ala | Ser | Pro | Leu | Leu | Ala | Pro | Pro | Gln | Pro | Gln | Ala | Val | Leu | Ala |
| | | | | 2460 | | | | | 2465 | | | | | 2470 |
| cct | gaa | gcc | cca | cct | gtg | gcg | gca | ggc | gtg | ggg | gct | gtg | ctt | gcc | 7485 |
| Pro | Glu | Ala | Pro | Pro | Val | Ala | Ala | Gly | Val | Gly | Ala | Val | Leu | Ala |
| | | | | 2475 | | | | | 2480 | | | | | 2485 |
| gct | gga | gca | ctg | ctt | ggc | ttg | gtg | gcc | gga | gct | ctc | tac | ctc | cgt | 7530 |
| Ala | Gly | Ala | Leu | Leu | Gly | Leu | Val | Ala | Gly | Ala | Leu | Tyr | Leu | Arg |
| | | | | 2490 | | | | | 2495 | | | | | 2500 |
| gcc | cga | ggc | aag | ccc | acg | ggc | ttt | ggc | ttc | tct | gcc | ttc | cag | gcg | 7575 |
| Ala | Arg | Gly | Lys | Pro | Thr | Gly | Phe | Gly | Phe | Ser | Ala | Phe | Gln | Ala |
| | | | | 2505 | | | | | 2510 | | | | | 2515 |
| gaa | gat | gat | gct | gac | gac | gac | ttc | tca | ccg | tgg | caa | gaa | ggg | acc | 7620 |
| Glu | Asp | Asp | Ala | Asp | Asp | Asp | Phe | Ser | Pro | Trp | Gln | Glu | Gly | Thr |
| | | | | 2520 | | | | | 2525 | | | | | 2530 |
| aac | ccc | acc | ctg | gtc | tct | gtc | ccc | aac | cct | gtc | ttt | ggc | agc | gac | 7665 |
| Asn | Pro | Thr | Leu | Val | Ser | Val | Pro | Asn | Pro | Val | Phe | Gly | Ser | Asp |
| | | | | 2535 | | | | | 2540 | | | | | 2545 |
| acc | ttt | tgt | gaa | ccc | ttc | gat | gac | tca | ctg | ctg | gag | gag | gac | ttc | 7710 |
| Thr | Phe | Cys | Glu | Pro | Phe | Asp | Asp | Ser | Leu | Leu | Glu | Glu | Asp | Phe |
| | | | | 2550 | | | | | 2555 | | | | | 2560 |
| cct | gac | acc | cag | agg | atc | ctc | aca | gtc | aag | tgacgaggct | ggggctgaaa | 7760 |
| Pro | Asp | Thr | Gln | Arg | Ile | Leu | Thr | Val | Lys | | |
| | | | | 2565 | | | | | 2570 | | |
| gcagaagcat | gcacagggag | gagaccactt | ttattgcttg | tctgggtgga | tggggcagga | 7820 |
| ggggctgagg | gcctgtccca | gacaataaag | tgccctcagc | ggatgtgggc | catgtcacc | 7879 |